United States Patent
Hummer et al.

(10) Patent No.: US 11,869,329 B2
(45) Date of Patent: Jan. 9, 2024

(54) MONITORING SYSTEM FOR USE WITH MOBILE COMMUNICATION DEVICE

(71) Applicants: Gregory J. Hummer, Shaker Heights, OH (US); Matthew Hummer, Shaker Heights, OH (US)

(72) Inventors: Gregory J. Hummer, Shaker Heights, OH (US); Matthew Hummer, Shaker Heights, OH (US)

(*) Notice: Subject to any disclaimer, the term of this patent is extended or adjusted under 35 U.S.C. 154(b) by 0 days.

(21) Appl. No.: 18/074,437

(22) Filed: Dec. 2, 2022

(65) Prior Publication Data
US 2023/0093999 A1 Mar. 30, 2023

Related U.S. Application Data

(63) Continuation-in-part of application No. 16/513,753, filed on Jul. 17, 2019, now Pat. No. 11,527,141, which is a continuation of application No. 15/891,410, filed on Feb. 8, 2018, now Pat. No. 10,395,503, which is a continuation of application No. 15/235,981, filed on Aug. 12, 2016, now Pat. No. 9,922,525.

(60) Provisional application No. 62/297,385, filed on Feb. 19, 2016, provisional application No. 62/205,012, filed on Aug. 14, 2015.

(51) Int. Cl.
| | |
|---|---|
| *G08B 21/12* | (2006.01) |
| *H04B 1/3888* | (2015.01) |
| *H04M 1/72412* | (2021.01) |
| *G08B 25/10* | (2006.01) |
| *G01N 33/00* | (2006.01) |
| *G01N 33/497* | (2006.01) |
| *H04M 1/21* | (2006.01) |

(52) U.S. Cl.
CPC .......... *G08B 21/12* (2013.01); *H04B 1/3888* (2013.01); *H04M 1/72412* (2021.01); *G01N 33/0009* (2013.01); *G01N 33/4972* (2013.01); *G08B 25/10* (2013.01); *H04M 1/21* (2013.01)

(58) Field of Classification Search
CPC ...... G08B 21/12; G08B 25/10; G08B 21/182; H04B 1/3888; H04M 1/72412; H04M 1/21; G01N 33/0009; G01N 33/4972
See application file for complete search history.

(56) References Cited

U.S. PATENT DOCUMENTS

| | | | | |
|---|---|---|---|---|
| 7,176,793 | B1 * | 2/2007 | Hummer | G08B 25/012 340/8.1 |
| 7,911,336 | B1 * | 3/2011 | Hummer | G08B 25/08 340/8.1 |
| 8,204,561 | B2 * | 6/2012 | Mongan | H04B 1/3888 455/575.8 |
| 8,323,193 | B2 * | 12/2012 | Skerl | A61B 5/14539 600/365 |
| 9,241,054 | B1 * | 1/2016 | Roberts | G01N 33/4972 |

(Continued)

*Primary Examiner* — Nay Tun
(74) *Attorney, Agent, or Firm* — Edmond DeFrank

(57) ABSTRACT

A monitoring system for monitoring, measuring and detecting analytes in an environment or in test samples from an environment. The monitoring system generates data in response to the presence of at least one analyte. The monitoring system is configured to communicate the data to an associated receiver such as personal communication device or the like for processing. The monitoring system can be in the form of a selectively attachable component.

19 Claims, 21 Drawing Sheets

(56) References Cited

U.S. PATENT DOCUMENTS

| | | | | |
|---|---|---|---|---|
| 2005/0245839 A1* | 11/2005 | Stivoric | ............ | A61B 10/0012 |
| | | | | 374/E1.004 |
| 2006/0143645 A1* | 6/2006 | Vock | ................... | A61B 5/0002 |
| | | | | 725/9 |
| 2013/0250845 A1* | 9/2013 | Greene | ................ | H04W 40/08 |
| | | | | 343/720 |
| 2014/0298927 A1* | 10/2014 | Allin | ...................... | A61B 5/002 |
| | | | | 73/865.8 |
| 2014/0336474 A1* | 11/2014 | Arbabian | .............. | A61B 5/686 |
| | | | | 600/300 |
| 2015/0180525 A1* | 6/2015 | Chen | .................... | H04B 5/0031 |
| | | | | 455/575.8 |
| 2015/0351648 A1* | 12/2015 | Harvey | ................. | A61B 5/076 |
| | | | | 600/561 |
| 2015/0363280 A1* | 12/2015 | Yeager | .................... | A61B 5/00 |
| | | | | 711/104 |
| 2016/0166438 A1* | 6/2016 | Rovaniemi | ............. | A61F 13/42 |
| | | | | 493/320 |
| 2016/0209441 A1* | 7/2016 | Mazzeo | ................ | G06F 3/0447 |
| 2016/0255878 A1* | 9/2016 | Huang | ................... | A24F 40/51 |
| 2018/0077763 A1* | 3/2018 | Schneider | ................ | H05B 6/66 |
| 2022/0091068 A1* | 3/2022 | Irving | .................. | A61B 5/1455 |
| 2022/0219169 A1* | 7/2022 | Alcorn | ................ | B01L 3/50273 |

* cited by examiner

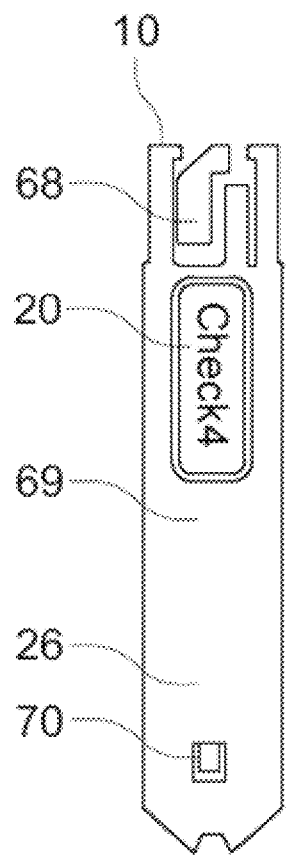 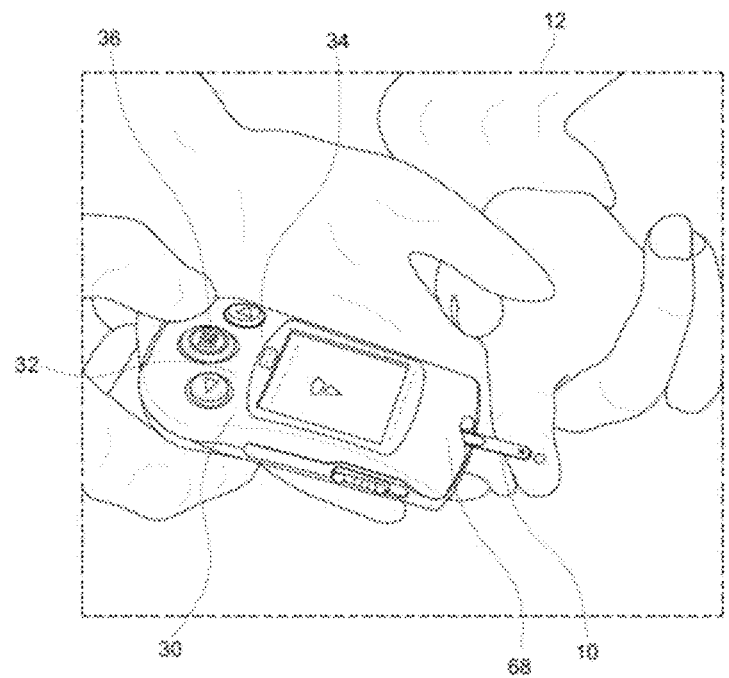
FIG. 13A         FIG. 13B

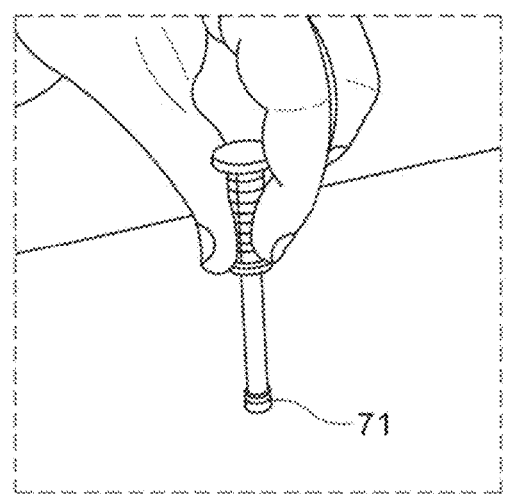
FIG. 17A
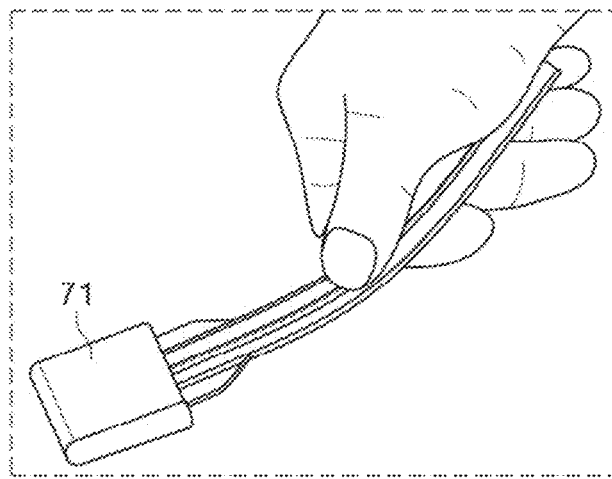
FIG. 17B
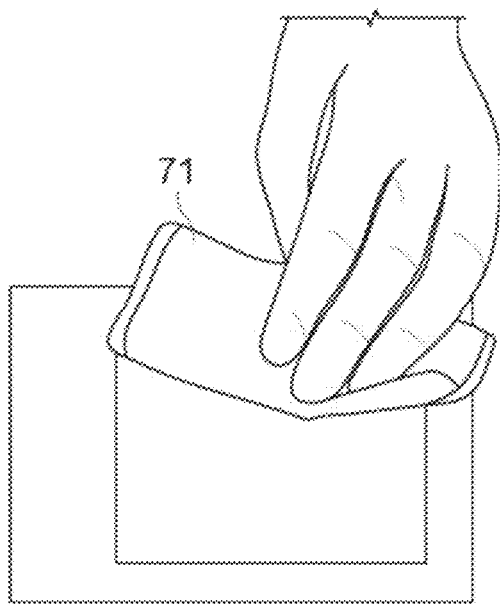
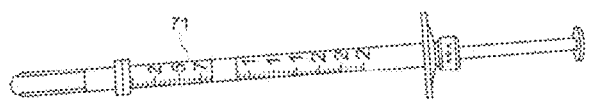
FIG. 17C  FIG. 17D

MONITORING SYSTEM FOR USE WITH MOBILE COMMUNICATION DEVICE

CROSS REFERENCE TO RELATED PATENTS AND APPLICATIONS

This application is a continuation-in-part of and claims priority to and the benefit of U.S. application Ser. No. 16/513,753 filed Jul. 17, 2019, entitled "MONITORING SYSTEM FOR USE WITH MOBILE COMMUNICATION DEVICE", by Gregory J. Hummer, which is a continuation of U.S. application Ser. No. 15/891,410, filed Feb. 8, 2018, entitled "MONITORING SYSTEM FOR USE WITH MOBILE COMMUNICATION DEVICE", by Gregory J. Hummer, which is a continuation of Ser. No. 15/235,981, entitled "MONITORING SYSTEM FOR USE WITH MOBILE COMMUNICATION DEVICE", by Gregory J. Hummer, filed Aug. 12, 2016, which claims the benefit of U.S. Provisional application Ser. No. 62/297,385 filed Feb. 19, 2016 and U.S. Provisional application Ser. No. 62/205,012 filed Aug. 14, 2015.

BACKGROUND

Disease and illness present a significant threat to humans and animals. Rapid diagnosis of disease and illness can be accomplished by monitoring and measuring analytes, mitigating serious disease, illness and even death. Real-time monitoring and rapid detection of pathogens, biomarkers and analytes is of great need for improving the health of humans and animals.

SUMMARY OF THE INVENTION

The present exemplary embodiment relates to systems and methods for detecting analytes. It finds particular application in conjunction with personal communication devices and/or other handheld or portable electronic devices and will be described with particular reference thereto. However, it is to be appreciated that the present exemplary embodiment is also amenable to other like applications.

BRIEF DESCRIPTION OF THE DRAWINGS

FIG. 13A shows for illustrative purposes an exemplary monitoring system with at least one of a connector, or a monitor/detector of one embodiment.

FIG. 13B shows for illustrative purposes an exemplary associated receiver that provides use of at least one component including a power source to the monitor of one embodiment.

FIG. 17A shows for illustrative purposes an exemplary monitoring system integrated into a strip that is placed at the source of a test sample of one embodiment.

FIG. 17B shows for illustrative purposes an example of sampling a medium sized surface area with the tip of the sample collector of one embodiment.

FIG. 17C shows for illustrative purposes sampling a large sized surface area using a sample collector of one embodiment.

FIG. 17D shows for illustrative purposes an example of sampling liquid from an environment or surface with a syringe used to collect bodily fluid samples of one embodiment.

BRIEF DESCRIPTION

Figure 1:
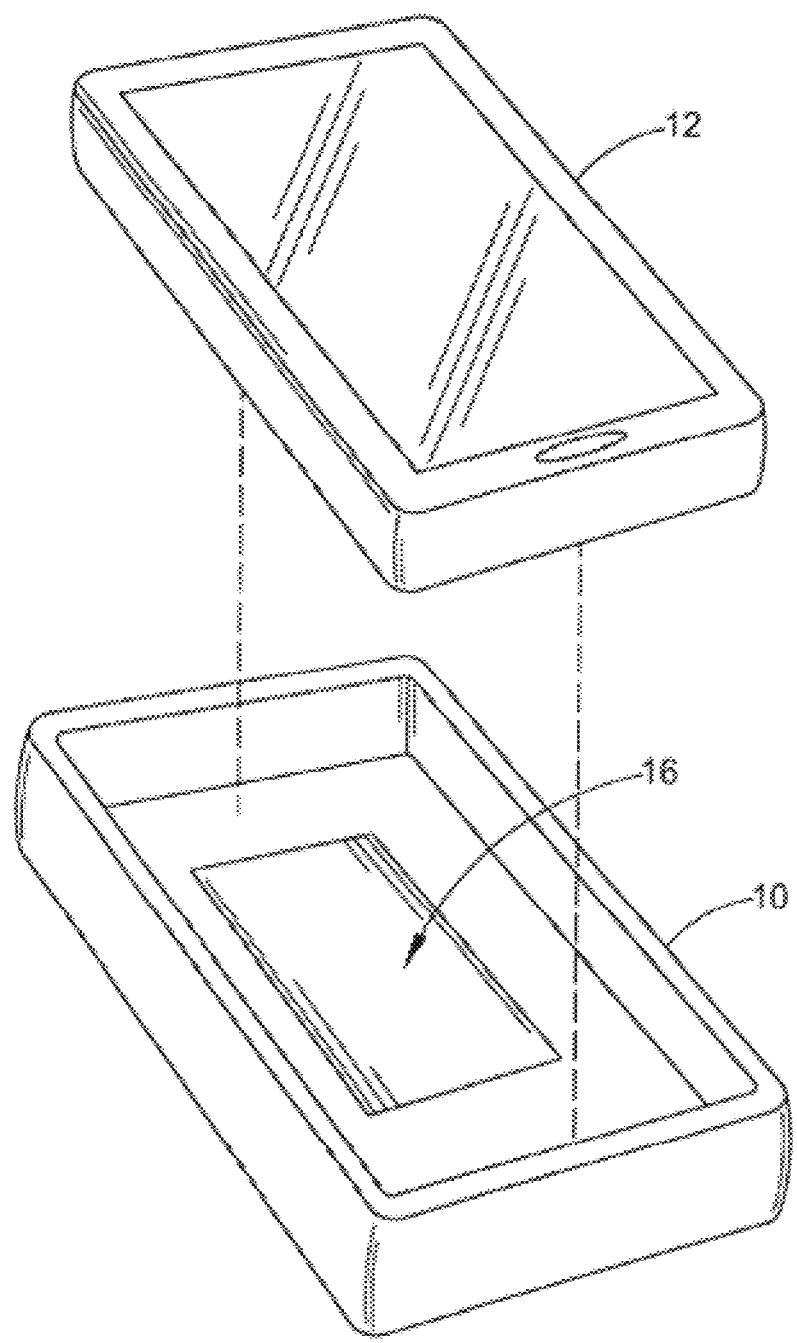
FIG. 1 illustrates a perspective view of an exemplary communication device and removable component of one embodiment.

There is a need for real-time monitoring and rapid detection of viruses, biomarkers and analytes in bodily fluid samples. This disclosure presents devices, systems and methods for monitoring and detecting analytes present on at least one surface, wherein the surface is a human tongue, dental (tooth) and bodily or non-bodily surface. The monitoring system is configured to collect samples from environments or surfaces and generate data in response to the presence or absence of at least one analyte or concentration of at least one analyte from the environment or surface. The monitoring system is configured to communicate the data to an associated receiver, wherein the associated receiver is a personal communication device, smart phone, smart watch, smart device, connected device, smart infrastructure, smart appliance, smart refrigerator, smart freezer, mobile device, wearable or like electronic device for processing. The monitoring system can be in the form of a selectively attachable component.

The terms herein "cell phone", "associated receiver", "personal communication device", "smart phone", "smart watch", "smart appliance", "smart device", "smart infrastructure", "smart equipment", "smart thermostat", "smart doorbell", "smart lock", "smart band", "smart glasses", "smart textile", "smart material", "connected device", "connected vehicle", "drone", "unmanned aerial vehicle", "unmanned ground vehicle", "unmanned undersea vehicle", "robot", "connected material", "connected equipment", "mobile device", "electronic device", "wearable", "implantable", "digital device" and "like electronic device" can be used without any change in meaning.

The terms herein "chemicals", "warfare agents", "nerve gases", "biological materials", "gases", "drugs", "narcotics", "explosives", "germ agents", "mycotoxins", "toxins", "viruses", "bacteria", "fungi", "protozoa", "worms", "proteins", "prions", "biomarkers", "amino acids", "nano-bodies", "aptamers", "nucleic acids", "DNA", "A-DNA", "B-DNA", "C-DNA", "D-DNA", "Z-DNA", "cfDNA", "ctDNA", "RNA", "mRNA", "tRNA", "rRNA", "molecules", "analytes" "monomers", "polymers", "large molecules", "small molecules", "organic molecules", "polar molecules", "non-polar molecules", "nucleotides", "amino acids", "lipids", "fatty acids", "peptides", "carbohydrates", "monosaccharides", "polysaccharides", "organelles" are used as targets of detection. Analyte targets can include any of the targets above.

Implementing real-time monitoring and rapid detection systems of analytes on surfaces and in environments presents unique challenges both in ensuring proper positioning of the detector and ensuring adequate flow of sample or adequate sample volume to the sensors. Aspects of the present disclosure overcome one or more of such challenges.

In accordance with one embodiment of the present disclosure, a monitoring system for monitoring an environment on a surface is disclosed. The monitoring system is operative to generate data in response to the presence of at least one analyte on the surface or in a sample from a surface and communicate the data to an associated personal communication device for processing, the monitoring system being selectively attachable to the associated personal communication device.

The monitoring system can include a detector component, communication circuitry and a power source operatively coupled to the detector component and the communication circuitry for supplying power thereto, and the communication circuitry can be configured to transmit data through a wire or wirelessly in response to detection of at least one analyte by the detector component. The power source can be at least one of, wherein the power source is a battery, a photovoltaic cell or an antenna for receiving electromagnetic energy. The monitoring system can be disposed of in a protective case or component of a personal communication device. The protective case or component of the personal communication device can be selectively attachable to an associated personal communication device. At least one of the detector components, communication circuitry or power source can be part of a removable/replaceable module selectively attachable to the protective case or component of the personal communication device.

In accordance with another embodiment, an assembly comprises a personal communication device having a processor and communication circuitry, and a device selectively attached to the personal communication device and having a monitoring system for monitoring an environment such as surfaces or samples from surfaces, the monitoring system operative to generate data in response to the presence of at least one analyte in the environment or sample from the environment and communicate the data to the personal communication device. The processor of the personal communication device processes the data received from the device attached thereto to determine at least one of the kind or concentration of the at least one analyte in the environment or sample from the environment.

In another embodiment, the personal communication device can include a non-transitory computer readable medium for storing instructions causing the processor to execute an application for processing the data, the application configured to: receive the data from the device and analyze the data to detect one or more analyte signatures.

The device attached to the personal communication device, wherein the device is a protective case or selectively attachable component. The protective case can include a resilient material for cushioning the personal communication device. The monitoring system can include a detector component, communication circuitry and a power source. At least one of the detector components, communication circuitry or power source can be part of a removable/replaceable module selectively attachable to the protective case or component of the personal communication device. Wherein the power source is a battery, a photovoltaic cell or an antenna for receiving electromagnetic energy. Power can also be drawn from an associated personal communication device or electronic device.

In accordance with another aspect, a method of detecting an analyte comprises generating data with a device attached to a personal communication device or electronic device in general, the device having a monitoring system for monitoring an environment or samples from an environment, the monitoring system operative to generate data in response to the presence of at least one analyte in the environment or sample from the environment, communicating the data to a personal communication device, and analyzing the data with the personal communication device to detect one or more analyte signatures.

The method can further include selectively attaching and removing the device to/from the personal communication device or associated receiver. Communicating the data to the personal communication device can be performed wirelessly, such as by using at least one of satellite, GPS, paging, radar, radio frequency identification, infrared, broadcast radio, electromagnetic, microwave, WIFI, Bluetooth, NFC, mobile or other wireless communication protocol.

DETAILED DESCRIPTION

FIG. 1 illustrates a perspective view of an exemplary communication device and removable component of one embodiment. FIG. 1 shows an exemplary monitor for monitoring and detecting analyte compositions and is illustrated and identified generally by reference numeral 10. In this embodiment, the monitor 10 is in the form of a protective case for a cell phone 12 or other personal communications device (e.g., tablets, laptops, smart devices, connected device, connected equipment, connected vehicle, wearables, implantables etc.). It will be appreciated that the present disclosure is not limited to any particular case design or configuration, and that aspects of the disclosure can be embodied in a wide variety of protective cases as well as ornamental cases and/or other devices attachable to either such cases or directly to a personal communication device or like digital device. In other embodiments, aspects of the disclosure can be embodied in other types of accessories that may commonly be used with a cell phone or personal communications device. For example, wearable devices such as smart devices, smart watches, hearing aids, mouthpieces, smart jewelry (e.g., rings, earrings and other piercings) smart fabrics, tattoo sensors peripheral devices such as speakers, scanners, conveyors, appliances, equipment, vehicles, drones, infrastructure etc.

The cell phone 12 is configured to be received in and/or at least partially surrounded by the case 10 in any suitable fashion. In some arrangements, the case may be made of a resilient material that can be deformed to allow the cell phone 12 to be securely inserted and retained within the case. In other arrangements, the case can include a hard plastic two-piece frame between which the cell phone 12 is sandwiched. Again, a wide variety of case designs and types are envisioned. The case 10 further includes a monitor system, which in FIG. 1 is identified by reference numeral 16.

Figure 2:
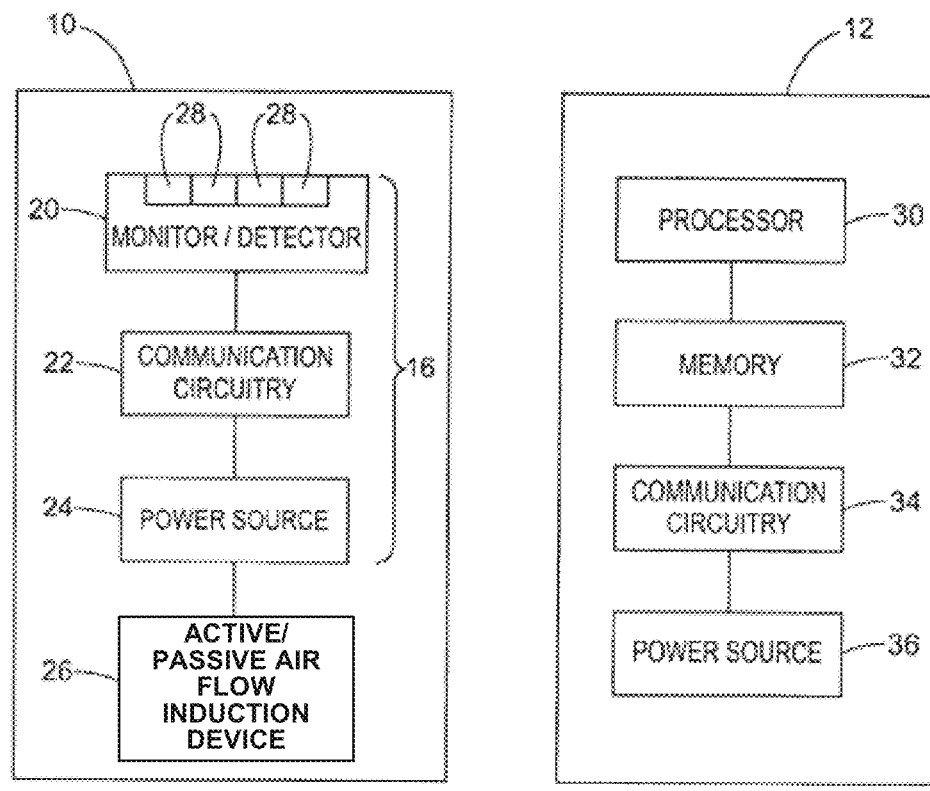
FIG. 2 illustrates a block diagram of an exemplary system of one embodiment.

FIG. 2 illustrates a block diagram of an exemplary system of one embodiment. FIG. 2 shows the monitor system 16 generally includes a monitor/detector component 20. One monitor/detector component that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector components can also be used in accordance with the present disclosure.

The monitor system further includes communication circuitry 22 and a power source 24. The communication circuitry 22, in one embodiment, includes at least one of a near field communication device, Bluetooth communication device, cellular, satellite, WIFI communication device, or any other suitable communication circuitry for establishing communications with the cell phone 12. The power source 24 can be a power supply such as a battery (lithium or other) mounted or otherwise contained within the case 10. In other embodiments, the power source 24 can be an antenna configured to receive energy wirelessly and supply the received energy to one or both of the monitor/detector component 20 and/or communication circuitry 22 such that no onboard battery is required for operation of the monitor system 16. In still other arrangements, the power source 24 can be a connector configured to couple with a port of the cell phone 12 to receive power from a power source of the cell phone 12.

An active or passive air flow induction device 26 can be provided for ensuring adequate and or continuous flow of air to the monitor 20. Such devices can include fans, micropumps, pumps, louvers, vacuums, vents, flow paths, magnets etc. An active induction device can be separately replaceable within the system and can include its own power supply. Alternatively, an active induction device can be configured to receive power from power source 24 of the monitoring system or the power source 36 of the cell phone 12.

It should be appreciated that the monitor/detector component 20 can comprise a plurality of sensors 28. The sensors 28 can be individually replaceable or can be replaced as a unit. Replacement of the sensors may be necessary due to sensor degradation. In other situations, a user may wish to detect certain analytes and will choose which sensors to install in the system. In one embodiment, the entire monitor system 16 is replaceable as a unit.

The sensors 28 may detect harmful materials, such as explosives, radioactive materials, harmful analytes, such as analyte warfare agents, nerve gases, biological materials, such as gases, anthrax and other germ warfare agents, narcotics and other illegal drugs, or combinations thereof. At least one of the sensors 28 can be configured for generating a signal which is indicative of the presence of a nitrogen-based explosive, such as trinitrotoluene (TNT) and/or a peroxide-based explosive, such as triacetone triperoxide (TATP) or hexamethylenetriperoxidediamine (HMTD), or a combination thereof, for example.

It will be appreciated that the sensors 28 are fabricated using any suitable method including printing. Among suitable printing methods are digital printing, flexographic printing, lithographic printing, offset printing, gravure printing, 3D printing, inkjet printing, aerosol printing, spin/spray coating printing, screen printing pad printing among other methods for printing conductive materials.

It will be appreciated that the monitor system 16 is configured to communicate with the cell phone 12. That is, the monitor system 16 collects data and transmits or otherwise shares the collected data with the cell phone 12 for processing. The cell phone 12 of the illustrated embodiment includes a processor 30, a memory 32, a communication circuitry 34, and a power source 36. It will be appreciated if the cell phone 12 can include a wide variety of additional components as is conventional. Such additional components can include a display device, input device, various sensors, and various antennas, etc.

Data collected by the monitor/detector 20 is transmitted via communication circuitry 22 to communication circuitry 34 of the cell phone 12. Other data, such as sensor state, status, performance data, sensor location and the like can also be transmitted to the cell phone 12. Any suitable manner of transmitting the data from the monitor system 16 to the cell phone 12 can be employed.

The data collected and transmitted by the monitoring system 16 is then processed by the phone to detect one or more analytes in accordance with one or more methods set forth in U.S. Pat. No. 8,629,770 to Hummer et al. and U.S. Pat. No. 7,176,793 to Hummer. To this end, suitable software for analyzing the data is stored in memory 32 of the cell phone 12. Other detection and/or analyzing methods and techniques may also be used in conjunction with aspects of the present disclosure.

In one embodiment, the software stored in memory 12 can be in the form of an application, or "app", that is downloaded from an app store or the like. The app can access other associated receivers known as the Cloud for processing and storing data generated by the monitor/detector 20. The app can be provided with various "signatures" of analytes. The signatures can be compared to the data generated by the monitor/detector 20 to determine whether the analyte signature was detected by the monitoring system 16. The app can be configured to be automatically updated with new signatures as the need to detect particular analytes as they arise. That is, it is possible to provide new and/or additional analyte signatures for the app to check against the data to detect specific analytes.

The app can further include features such as adjustable thresholds. For example, for some analytes and biomarkers that are routinely present in certain amounts and/or not generally considered dangerous below certain levels, the application can be configured to detect or trigger an alarm when a threshold amount is met or exceeded. For some analytes which are considered dangerous in any amount, the thresholds would not generally be adjustable.

The app can be further configured to, once an analyte or biomarker is detected, share the detection information. For example, the application can be configured to use the communication circuitry 34 to broadcast an alert (or generate a notification) via any suitable communications network (e.g., WIFI, NFC, Bluetooth, satellite, cell, etc.). The alert may be directly sent to other cell phones and/or personal communication devices in the area or may be sent to a server (or through a network) and then on to devices within a range of a given location. Accordingly, the application can be configured to use location information from a GPS chip, WIFI or any other location information available to the cell phone 12 to identify the location of the detected analyte.

The app can be configured to alert the authorities in the event certain analytes are detected. For example, the detection of any amount of sarin gas (or other analyte/biological weapon) can trigger information relating to the location, time, etc. of the detection to be forwarded to certain designated authorities for threat management/mitigation.

It should be appreciated that a network of devices having monitoring systems, each detecting a certain analyte, can be configured to share valuable data regarding the dispersion of the particular analyte. For example, devices in close proximity to each other and the point of origin of the analyte may detect a greater concentration of the analyte than devices further away from the point of origin. Using this data and an appropriate dispersion model, a point of origin can be calculated. This can allow responsive action to be taken more quickly than otherwise would be the case.

Similarly, the data (location, concentration, etc.) from a plurality of such devices can be used to predict dispersion of the analyte so that preemptive action can be taken to minimize exposure of humans to the detected analyte.

Providing the monitoring system 16 in a separate component that is attachable to a phone or other personal communication device has several advantages. For example, any and all such devices can become monitors/detectors upon the provision of a suitable case or other component. Accordingly, a consumer can decide whether to add the functionality. In addition, the orientation, location and other aspects of the positioning of the sensor elements within the case or other component can be standardized to provide more consistent detection as compared to placing the sensor elements within various different models of cell phones. This is because the myriad of phone manufacturers and models each have different space constraints that would dictate different available locations, orientations, etc. for the sensor elements within the phone. As such, some sensor elements would be in a better position within a respective phone to detect analytes than other phones. This can lead to widely varying detection accuracy between different phones exposed to the same concentration of a given analyte.

It should be appreciated that, although the monitoring system 16 is illustrated as part of a case 10, the monitoring system can also be provided as a separate unit attachable either directly to a cell phone or the like, or attachable to a case in which a cell phone is contained.

Figure 3:
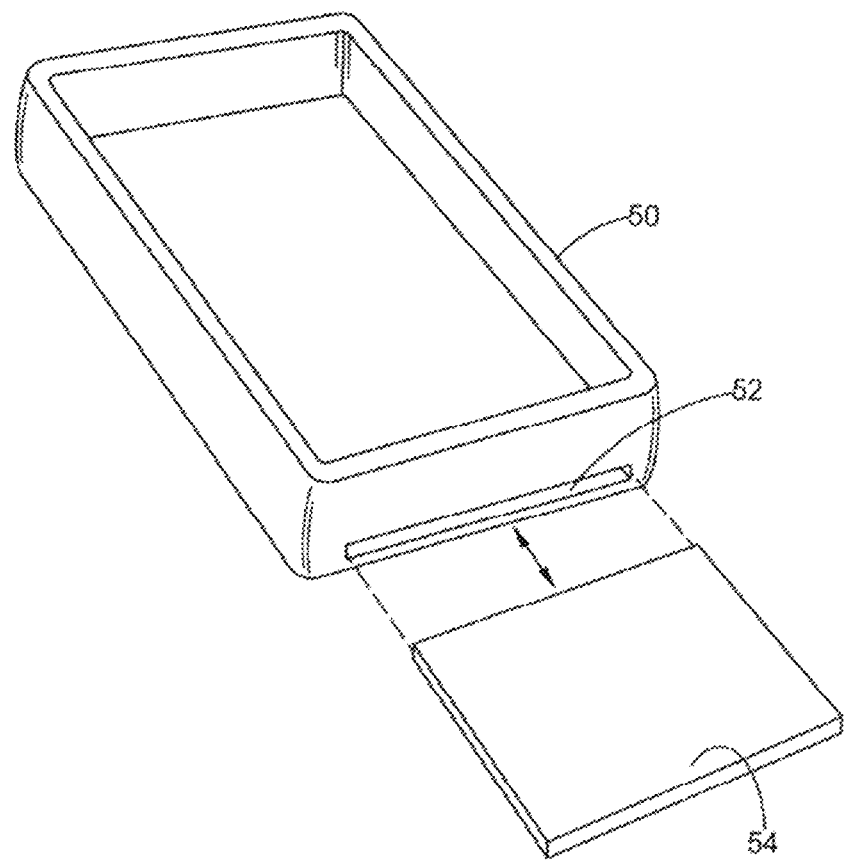
FIG. 3 illustrates another exemplary removable component of one embodiment.

FIG. 3 illustrates another exemplary removable component of one embodiment. With reference to FIG. 3, another exemplary embodiment is illustrated and includes a case for a personal communication device identified generally by reference numeral 50. In this embodiment, the case 50 is similar to the case 10 of FIG. 1 but further includes a slot 52 for receiving a removable and/or replaceable monitoring system 54. In one embodiment, the removable/replaceable component includes all of the components of the monitoring system such as a power source, monitor/detector components, and communications circuitry. In other embodiments, the removable/replaceable component can include only the sensors of the monitor/detector, only the power source, only the communication circuitry, or any combination thereof. The removable/replaceable component can be configured to "click-lock" in the slot 52 in a manner similar to an SD card or the like wherein the component is pressed into the slot until a latch engages to retain the component and then pressed further into the slot to release the latch for removal. It will be appreciated that there are a wide variety of ways to retain the removable component in the slot. A seal or weatherproof cap can be provided to prevent ingress of water or contaminants.

While the foregoing embodiments illustrate a monitoring system attachable to a personal communication device directly or via a protective case or the like, it should be appreciated that the monitoring system of the above-described embodiments can also link to the personal communication device without being physically attached thereto. Thus, the monitoring system can be provided as a standalone system to which the personal communication device can be configured to connect to perform the above-described functions.

Figure 4:
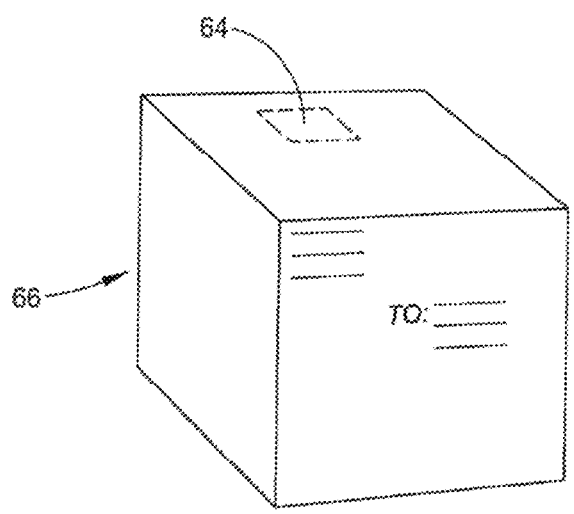
FIG. 4 illustrates an exemplary container including a monitoring system of one embodiment.

FIG. 4 illustrates an exemplary container including a monitoring system of one embodiment. For example, with reference to FIG. 4, a monitoring system 64 is provided in a separate container 66, such as a shipping box or the like. When the personal communication device is placed in proximity to the shipping box, the monitoring system 64 can be configured to connect a personal communication device, such as cell phone 12, and perform the above-described functionality. The monitoring system 64 can be placed inside the box, for detecting analytes carried within the box, for example. In other embodiments the monitoring system 64 can additionally or alternatively monitor for analytes outside of the box.

It should be appreciated that the monitoring system 64 can be configured to communicate with other devices besides (or in addition to) the personal communication device described above. Such devices can include scanners, conveyors, processors or other devices, equipment, vehicles or infrastructure adapted to connect and receive data from a plurality of such monitoring systems disposed in a plurality of respective containers.

In one example, a scanning device can be associated with a conveyor system of a parcel service for scanning packages by communicating with monitoring systems associated with the packages as they advance through a shipping facility. In another example, the monitoring devices of the present disclosure can be associated with luggage (or other airline or common carrier freight). It will be appreciated that a wide variety of applications for the technology of the present disclosure are contemplated.

In some embodiments, it can be advantageous to include active and/or passive air flow inducing devices for ensuring sufficient air flow across the sensors. This can be particularly advantageous for applications wherein the sensors are in a fixed location, such as within a cargo hold or other location. Suitable devices can include fans or micropumps or vacuums for displacing air across and/or adjacent to a sensor installation. In some applications, louvers or vent openings can be positioned to maximize air flow to the sensor. Increasing air flow can make detection of certain analytes more efficient.

It should be appreciated that the monitoring system 16 of FIG. 2 of the present disclosure can be configured to activate sensors 28 only when connected to a personal communication device or the like. In such configuration, the monitoring system generally lies dormant until such time as a connection is made with a remote device. The monitoring system 16 of FIG. 2 may then begin sensing for one or more analytes and transmitting data to the remote device.

In another configuration, the monitoring system 16 of FIG. 2 may be configured to periodically activate to sense for the presence or absence of one or more analytes regardless of whether the monitoring system 16 of FIG. 2 is connected to a remote device. In this case, once the monitoring system 16 of FIG. 2 connects to a remote device, all past data gathered by the monitoring system 16 of FIG. 2 can be transmitted to the remote device to provide a sensing history.

Turning to FIGS. 5-9, various applications of the exemplary monitoring system are illustrated.

Figure 5:
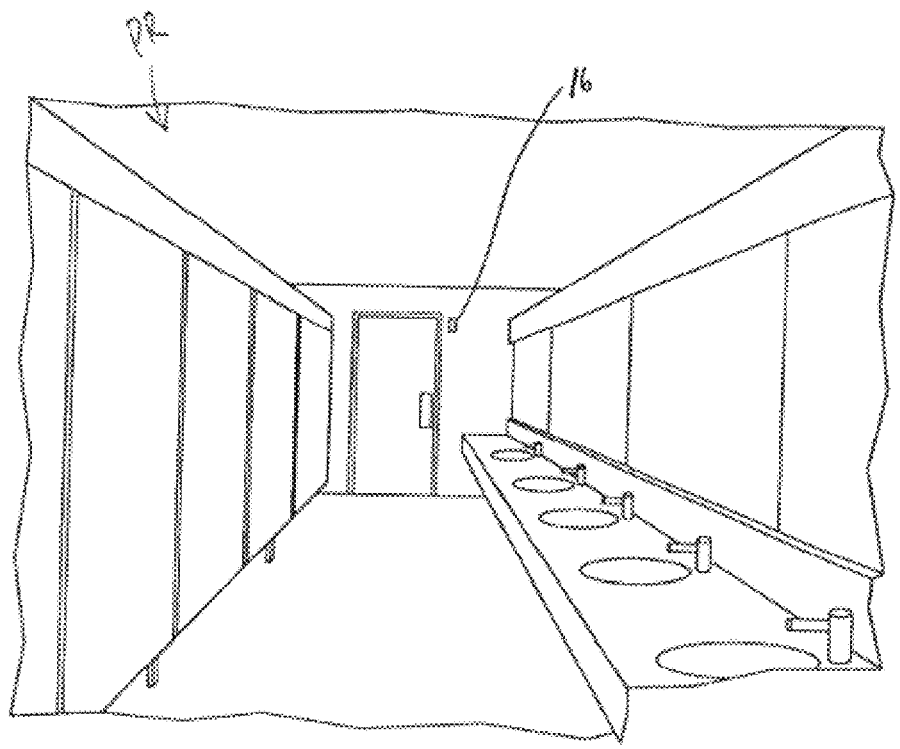
FIG. 5 illustrates an exemplary public space in which the monitoring system is configured to monitor of one embodiment.

FIG. 5 illustrates an exemplary public space in which the monitoring system is configured to monitor of one embodiment. In FIG. 5, a monitoring system 16 is deployed in a public restroom facility PR. The monitoring system 16 can be placed near a door in a position to where air flow into/out of the facility may generally be optimized. The monitoring system 16 could also be incorporated into an air duct of the facility. The monitoring system 16 can be configured to communicate with one or more handheld devices or can establish a permanent or semi-permanent connection to existing communication infrastructure, such as WIFI or the like.

Figure 6:
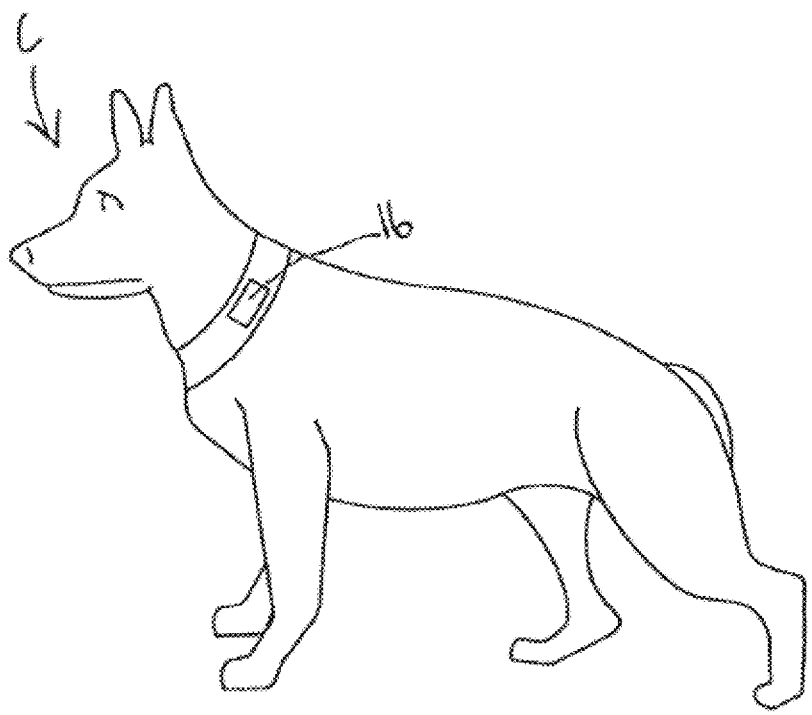
FIG. 6. illustrates an exemplary monitoring system integrated into a collar of a law enforcement canine of one embodiment.

FIG. 6. illustrates an exemplary monitoring system integrated into a collar of a law enforcement canine of one embodiment. In FIG. 6, a monitoring system 16 is integrated into the collar of a law enforcement canine C. It will be appreciated that movement of the canine C will cause air to circulate around the monitoring system 16 to enhance sensing capabilities. In addition, the canine can be instructed to enter certain spaces for inspection and/or sampling of the air that would generally not be accessible by other methods. In addition to mounting on a canine, the monitoring system can be mounted on other mobile platforms such as robots, drones or unmanned or manned vehicles.

Figure 7:
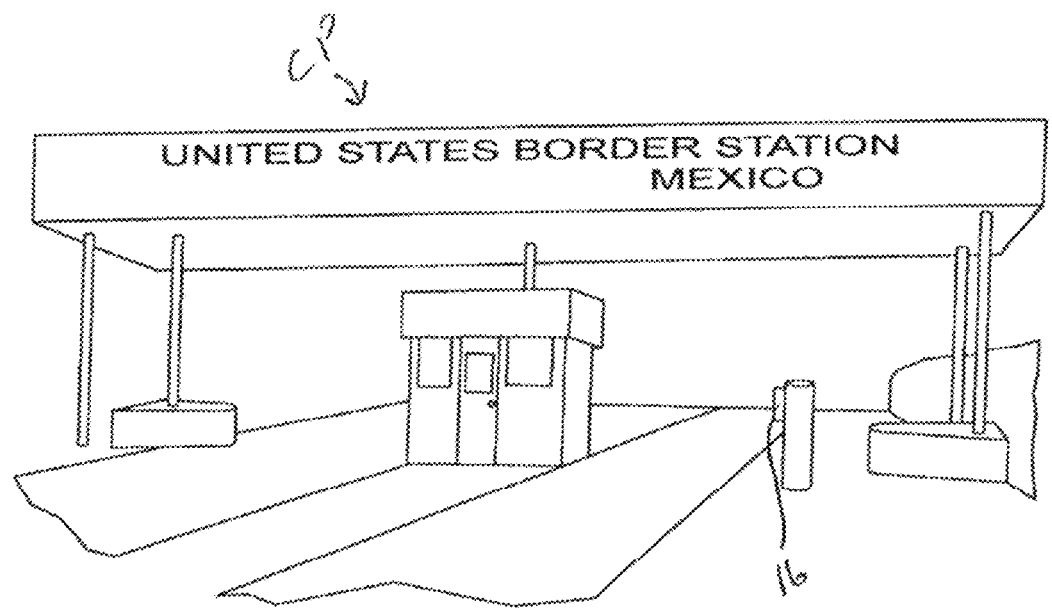
FIG. 7 illustrates another exemplary public space in which the monitoring system is configured to monitor of one embodiment.

FIG. 7 illustrates another exemplary public space in which the monitoring system is configured to monitor of one embodiment. FIG. 7 illustrates a monitoring system 16 in a customs and/or border patrol checkpoint CP. It will be appreciated if a plurality of monitoring systems can be deployed in suitable locations throughout the checkpoint. In the illustrated embodiment, the monitoring system is shown on a post adjacent to a vehicle travel path. It will be appreciated that a wide variety of applications for the technology of the present disclosure are contemplated for security screening at events and travel and shipping terminals among other situations where screening is conducted.

Figure 8:
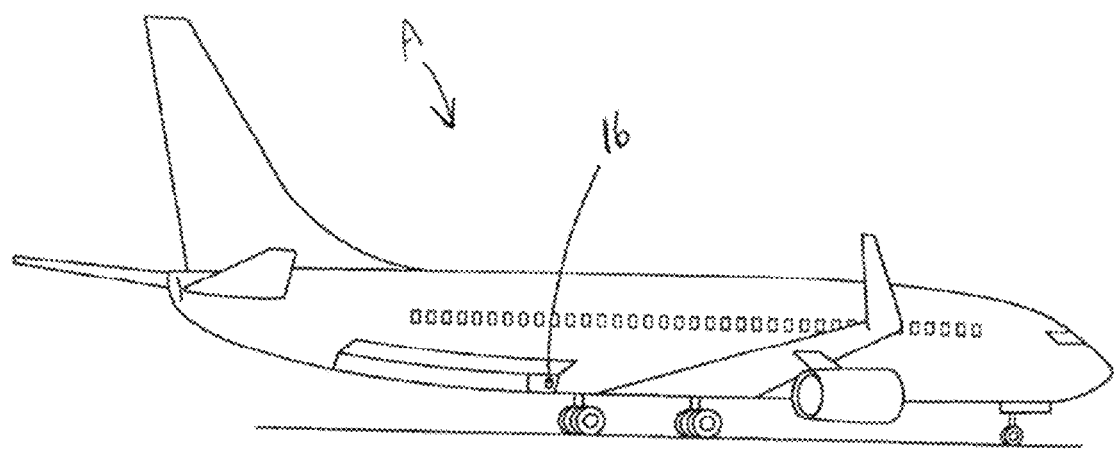
FIG. 8 illustrates an exemplary monitoring system integrated into a cargo hold of an aircraft of one embodiment.

FIG. 8 illustrates an exemplary monitoring system integrated into a cargo hold of an aircraft of one embodiment. FIG. 8 illustrates a monitoring system 16 in a cargo hold of an aircraft A, such as a commercial airliner. In other embodiments, the monitor 10 of FIG. 1 is deployed in passenger areas of an aircraft A. For example, the monitor 10 of FIG. 1 can be placed in overhead storage bins, near seats or other aircraft components and in airflow ducts of the aircraft A.

Figure 9:
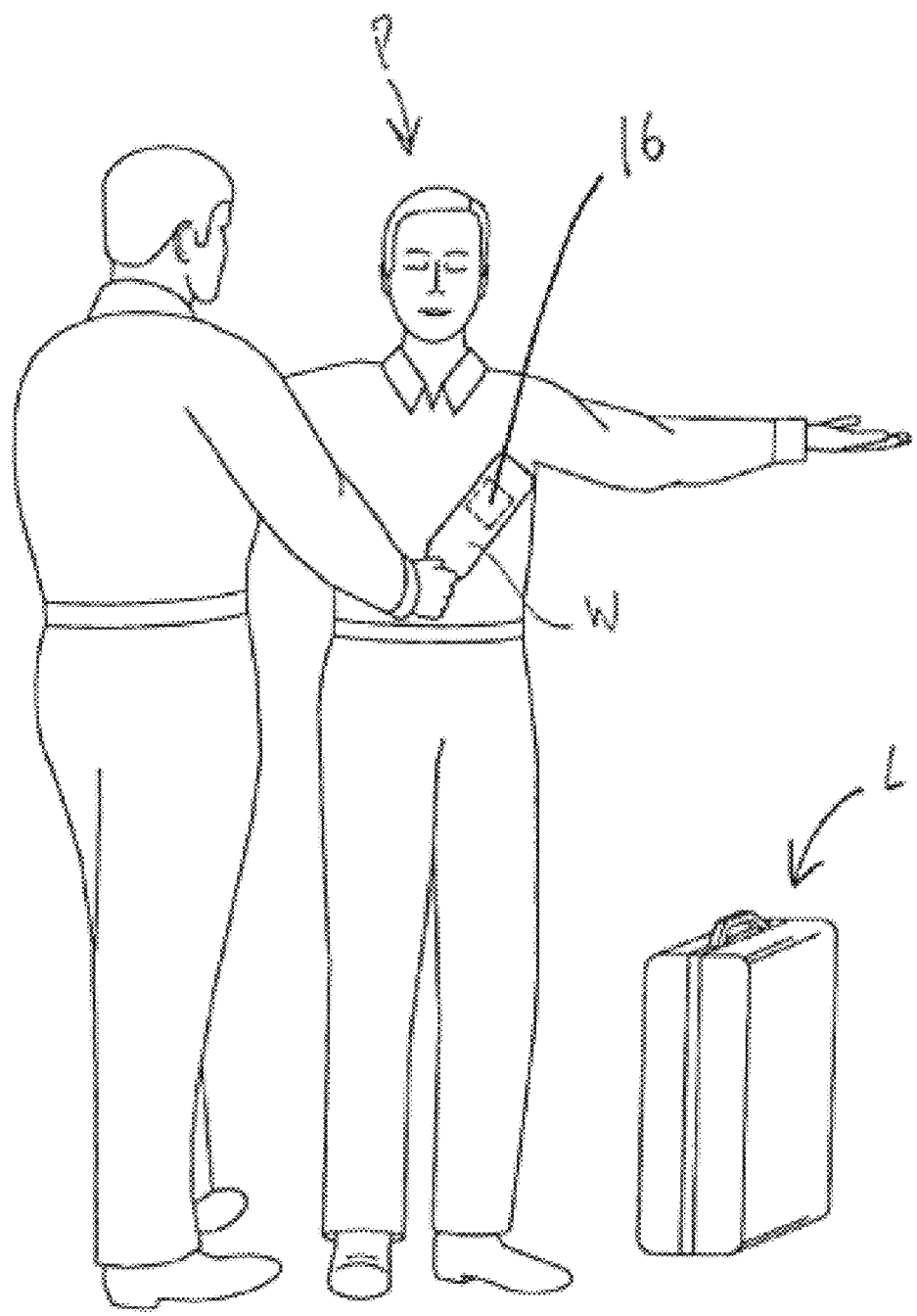
FIG. 9 illustrates an exemplary monitoring system integrated into a handheld wand for scanning passengers and/or luggage of one embodiment.

FIG. 9 illustrates an exemplary monitoring system integrated into a handheld wand for scanning passengers and/or luggage of one embodiment. FIG. 9 illustrates a monitoring system 16 integrated into a handheld wand W for manually scanning/sampling a passenger P and the passenger's luggage L. It will be appreciated that the monitoring system 16 can be incorporated into existing wands, such as metal detector wands typically used by security personnel for scanning passengers, luggage and cargo at airports or other venues.

Figure 10:
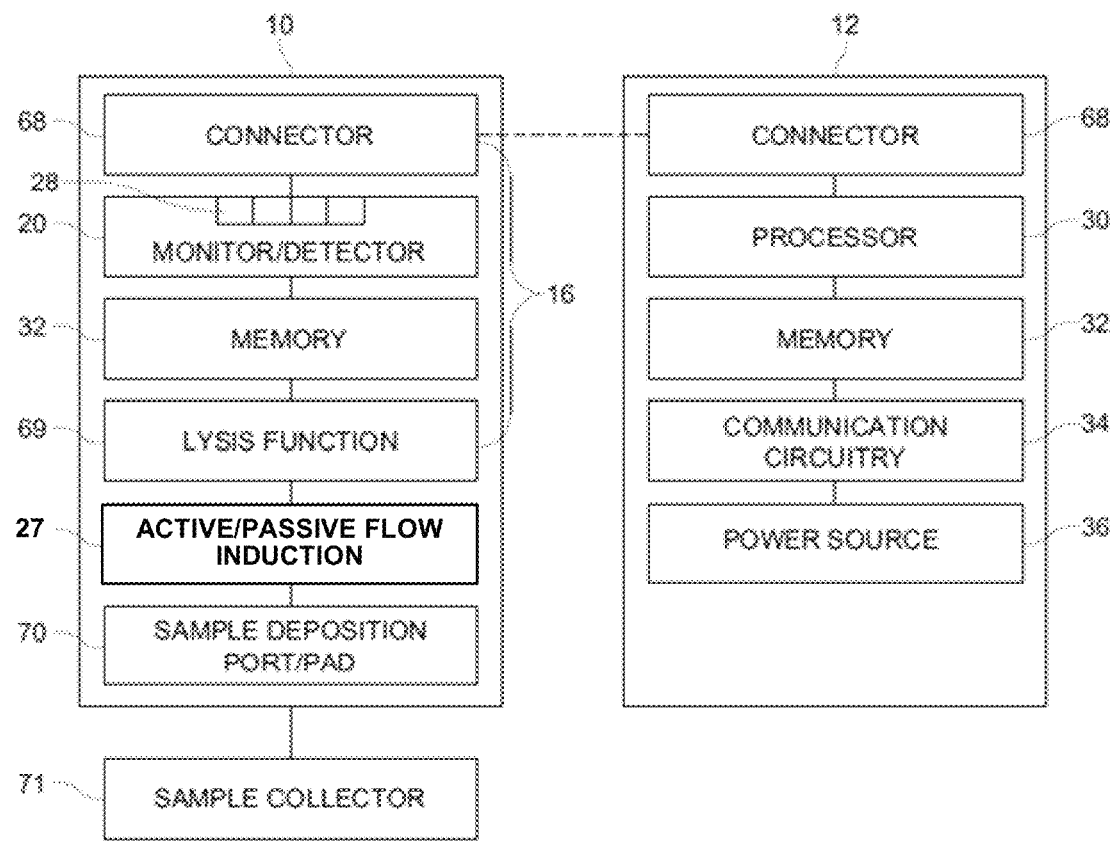
FIG. 10 shows a block diagram of an overview of an exemplary monitoring system integrated into a device for testing samples with a lysis function of one embodiment.

FIG. 10 shows a block diagram of an overview of an exemplary monitoring system integrated into a device for testing samples of one embodiment. The monitoring system comprising at least one of a connector, monitor/detector, memory and lysis function. FIG. 10 shows an exemplary monitor for monitoring an environment or measuring a sample from an environment is illustrated and identified generally by reference numeral 10. The exemplary embodiment involves applying the monitor/detector 20 directly on surfaces of environments or to samples from environments. In some arrangements the surface could be a body part or component attached to a body. In other arrangements the surface could be a surgical instrument or surgical material or surgical surface. In yet other arrangements the surface could be surfaces of any material or substance of an environment that encounters an analyte to be detected or measured. It will be appreciated that a wide variety of applications involving surfaces related to medical procedures, food processing, pharmaceutical production, consumer product manufacturing, freight, heating, ventilation, and air conditioning (HVAC) and potable water are contemplated.

With reference to FIG. 10, the monitor 10 generally includes a monitoring system 16 comprising a connector 68, monitor/detector 20, memory 32 and lysis function 69. In other embodiments, a lysis function 69 may not be included because not all target analytes require the lysis function for detection. Therefore, the monitoring system 16 can also include a lysis function 69 when necessary. In the exemplary embodiment, the monitor 10 further comprises an active/passive flow induction 27, sample deposition port/pad 70. It should be appreciated that some embodiments may not require an active/passive flow induction 27 and some embodiments would require a sample collector deposition port or a sample collection pad. In reference to the embodiments that include a sample collector deposition port, an associated sample collector 71 would also be required. The sample collector 71 mates with the sample collector deposition port 70 such that adequate sample volume is transferred from the sample collector 71 to monitor/detector 20 for monitoring and measuring analyte concentrations.

One monitor/detector component that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector components can also be used in accordance with the present disclosure. These types can include, but are not limited to: biosensors, electrochemical sensors, nano-sensors, Van der Waal material sensors, chemoresistors, field-effect transistor (FET) sensors, nanoparticle sensors, allotropes of carbon sensors, nanotube sensors, graphene sensors, Mxene sensors, impedimetric sensors, cyclic voltammetry, chronoamperometry, chronopotentiometry, amperometric, microelectrochemical systems (MEMS) and/or Nanoelectromechanical systems (NEMS) can be used. In some examples, quantum dots or allotropes of carbon quantum dots can be used. In still other examples, metal oxide semiconductor, infrared sensor (nondispersive), thermal sensor (pellitor), photoionization (PID), hybrid and nanostructures, Quartz Microbalance, and/or. It will be appreciated that the present disclosure is not limited to any particular type of detector or sensor configuration, and that aspects of the disclosure can be embodied in a wide variety of monitors or detectors or sensors.

The associated receiver 12 generally includes a connector 68, processor 30, memory 32, communication circuitry 34 and a power source 36. In some embodiments, the associated receiver 12 may not have memory 32 if the memory 32 is part of the monitor 10. In other embodiments, the monitor 10 has a memory 32 and the associated receiver 12 has a memory 32.

The communication circuitry 34, in one embodiment, includes at least one of a near field communication device, Bluetooth communication device, WIFI communication device, cellular, satellite or any other suitable communication circuitry for establishing communications with the associated receiver 12. The power source 36 can be a power supply such as a battery (lithium or other) mounted or otherwise contained within the associated receiver 12. In other embodiments, the power source 36 can be an antenna configured to receive energy wirelessly and supply the received energy to one or both of the monitor/detector component 20 and/or communication circuitry 34 such that no onboard battery is required for operation of the monitor system 16 of FIG. 2. In still other arrangements, the power source 36 can be a connector configured to couple with a port of the cell phone 12 or associated receiver to receive power from a power source of the cell phone 12. In this embodiment, the monitoring system 16 of FIG. 2 is configured to use the communication circuitry 34 and power source 36 of the phone 12 or associated receiver, such that the monitoring system 16 of FIG. 2 need only to comprise of the connector 68, monitor/detector 20, memory 32 and lysis function 69. It should be appreciated that in some embodiments, the lysis function may not be required. In other embodiments, the memory 32 of the monitor 10 is instead part of the associated receiver 12. In other embodiments, as shown in FIG. 2, the monitoring system has its own power source 24.

The monitoring system can further include a lysing function 69. Cellular lysing, also known as cellular disruption, which is a method in which the outer boundary or cell membrane is broken down or destroyed to release intercellular materials or nucleic acids such as DNA, RNA, protein, or organelles from a cell. The general methods of breaking down the membrane of a cell include mechanical and non-mechanical methods. Mechanical methods include liquid homogenization, high pressure homogenization, high frequency sound waves (sonication), thermal treatment, manual grinding, or bead mill. Non-mechanical methods fall into three categories, physical, chemical and biological. Physical methods include heating, osmotic shock, or cavitation. Chemical methods include alkaline and detergents, while biological methods cover the use of enzymes and viral. A lysis function 69 would only be included in the monitor 10, when required.

An active or passive flow induction device 26 can be provided for ensuring adequate and or continuous flow of air or fluid or other substance to the monitor/detector 20. Such devices can include housings, fluidic paths, fluidic devices, fans, magnets, vacuums, micropumps, pumps, louvers, vents etc. It will be appreciated that a wide variety of active or passive flow induction devices can be utilized.

An active induction device can be separately replaceable within the system and can include its own power supply. Alternatively, an active induction device can be configured to receive power from the power supply 24 of the monitoring system and/or the power source 36 of the associated receiver 12. An active/passive flow induction 27 would only be included in the monitor 10 when required.

In some embodiments, the monitoring system further includes a sample collector 71. It will be appreciated that the present disclosure is not limited to a particular sample collection configuration. For example, in some embodiments, bodily fluids (blood, semen, skin cells, tissue, organs, muscle, brain cells, bone, teeth, hair saliva, mucus, perspiration, tears, fingernails, urine, feces and other bodily fluid) will be sampled and tested. Other embodiments include testing fluids such as water for target analytes or concentrations of target analytes. A particular example includes testing water from air-conditioning units, faucets, pipes, pools, spas, showers and other water-related devices for contaminates, bacteria, and other analytes. In some embodiments the monitor/detector 20 or the plurality of sensors 28 is placed in an environment directly in contact with the source of the sample and not requiring a sample collection process.

It should be appreciated that the monitor/detector 20 component can comprise a plurality of sensors 28. The sensors 28 can be individually replaceable or can be replaced as a unit. Replacement of the sensors may be necessary due to sensor degradation. In other situations, a user may wish to detect certain analytes and will choose which sensors to install in the system. In one embodiment, the entire monitor system 16 of FIG. 2 is replaceable as a unit.

The sensors 28 may detect a wide range of analytes or concentrations of analytes such as nucleic acids, (DNA, RNA, mRNA tRNA, nucleotides: uracil, cytosine, thymine, adenine, and guanine), cell-free nucleic acids (cfDNA, cfRNA), circulating tumor nucleic acids (ctDNA and ctRNA), amino acids, nanobodies, aptamers, peptides, proteins, antibodies, nanobodies, blood gasses, carbohydrates, cells, electrolytes, enzymes, hemoglobin, hormones, lipids, metabolites, porphyrins, steroids, therapeutics, toxicology, tumor markers, biomarkers, viruses, microbes, vitamins, large molecules, small molecules and trace elements. While this is an exemplary list, it will be appreciated that the present disclosure is not limited to any particular chemical or analyte, rather shall encompass all analytes for which chemical composition can be monitored, measured or detected.

It will be appreciated that the monitor system 16 of FIG. 2 is configured to communicate with the associated receiver 12 that can be in the form of a smartphone. That is, the monitor system 16 of FIG. 2 collects data and transmits or otherwise shares the collected data with the smartphone 12 or associated receiver for processing. The smartphone 12 or associated receiver of the illustrated embodiment includes a connector 68, a processor 30, a memory 32, a communication circuitry 34, a power source 36. It will be appreciated if the smartphone 12 or associated receiver can include a wide variety of additional components as is conventional. Such additional components can include a display device, input device, various sensors, various antennas and various accessories etc.

Data collected by the monitor/detector 20 is transmitted via communication circuitry 22 to communication circuitry 34 of the smartphone 12 or associated receiver. Other data, such as sensor state, status, performance data, and the like can also be transmitted to the smartphone 12 or associated receiver. Any suitable manner of transmitting the data from the monitor system 16 to the smartphone 12 or associated receiver can be employed.

The data collected and transmitted by the monitoring system 16 of FIG. 2 is then processed by the phone or associated receiver to detect one or more analytes in accordance with one or more methods set forth in U.S. Pat. No. 8,629,770 to Hummer et al. and U.S. Pat. No. 7,176,793 to Hummer. To this end, suitable software for analyzing the data is stored in memory 32 of the cell phone 12 or associated receiver. Other detection and/or analyzing methods and techniques may also be used in conjunction with aspects of the present disclosure.

In one embodiment, the software stored in memory 32 can be in the form of an application, or "app", that is downloaded from an app store or the like. The app can be provided with various algorithms for determining a test result. The algorithms can determine whether the analyte was detected by the monitoring system 16 of FIG. 2. The app can be configured to be automatically updated with new algorithms as the need to detect particular analytes arises. That is, it is possible to provide new and/or additional algorithms for the app to check against the data to detect specific analytes. In some cases, the software stored in memory 32 of the app can be programmed to detect multiple analytes in a single test sample, whereby the sample comes into contact with a single sensor 28 or multiple sensors 28. The app can further include features such as adjustable thresholds. For example, some analytes are routinely present in certain amounts and not generally considered harmful below certain levels. In this particular embodiment, the application can be programmed to detect a threshold amount, providing notification when that threshold is met or exceeded. For some analytes which are considered harmful in any amount, the thresholds would not generally be adjustable.

The app can be further configured to, once test result data is generated, share the test data and information with a third party. For example, the application can be configured to use the communication circuitry 34 to share the test result data and information via any suitable communications network (e.g., WIFI, NFC, Bluetooth, cell, satellite etc.). In one embodiment, the app is configured to share test results with the APHL Informatics Messaging Services (AIMS) or like database serving as the official record of disease or illness. AIMS is a secure, cloud-based platform that accelerates the implementation of health messaging by providing shared services to aid in the visualization, interoperability, security, and hosting of electronic data. Examples of data currently exchanged through AIMS include: aggregated influenza test result data, vaccine-preventable disease reports, biological threat data, immunization data exchange among several public health jurisdictions, electronic laboratory reporting (ELR) between eligible hospitals and their respective jurisdictions, national quest ELR data to all jurisdictions, next generation sequencing (NGS) through the Advanced Molecular Detection (AMD) program, electronic case reporting (eCR) between providers and jurisdictions across the US. In other embodiments, the test result data and information can be shared with employers, insurers, health officials, authorities and any other third parties.

It should be appreciated that, although the monitor 10 is illustrated to comprise of a lysis function 69, active/passive flow induction 27 and a sample collector 71, the monitor 10 can also be configured such that a lysis function 69, active/passive flow induction 27 and sample collector 71 is not required.

Figure 11:
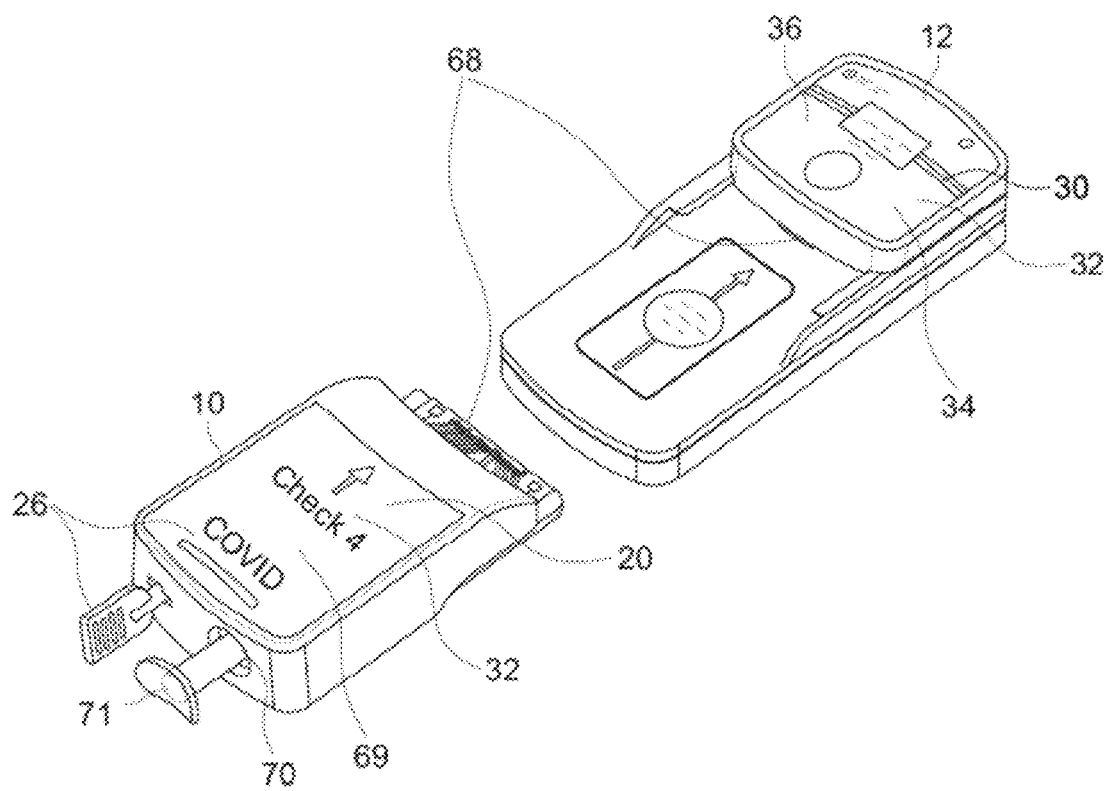
FIG. 11 shows for illustrative purposes an exemplary monitoring system and associated receiver to communicate the data to an associated personal communication device for processing of one embodiment.

FIG. 11 shows for illustrative purposes only an example of an exemplary monitoring system and associated receiver to communicate the data to an associated personal communication device for processing of one embodiment. The exemplary system is configured to communicate the data to an associated personal communication device or a like device for processing. The system comprising a monitor 10 and associated receiver 12. The monitor 10 is in the form of a cartridge and the associated receiver is in the form of a reader. It will be appreciated that the present disclosure is not limited to any particular cartridge design or configuration, and that aspects of the disclosure can be embodied in a wide variety of cartridges.

The monitor 10 in the form of a cartridge comprises of a connector 68, a monitor detector 20 having a plurality of sensors 28 of FIG. 2, a memory 32, a lysis function 69, an active/passive flow induction 27 and a sample collection deposition port 70. The embodiment also includes sample collector 71 such as a swab, syringe, collection assembly, collection vial or like collector.

The associated receiver 12 in the form of a reader, transmits data to a smartphone for processing results using a cloud-based software application. The associated receiver 12 comprising of a connector 68, a processor 30, memory 32, communication circuitry 34 and a power source 36.

Figure 12:
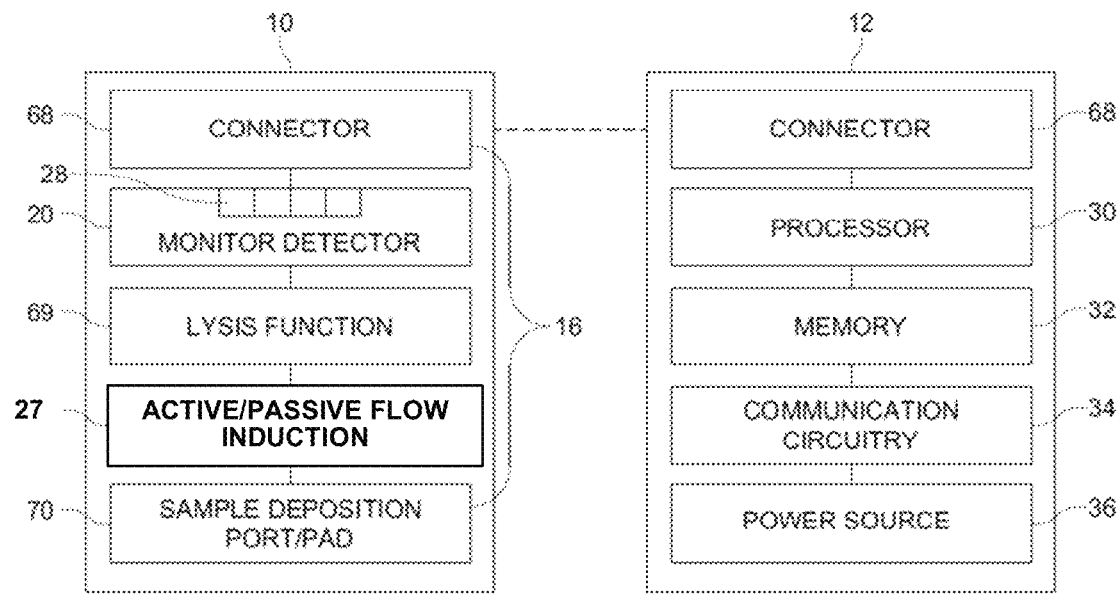
FIG. 12 shows a block diagram of an overview of an exemplary monitoring system integrated into a device for testing samples with at least one of an active/passive flow induction and sample deposition port/pad of one embodiment.

FIG. 12 shows a block diagram of an overview of an exemplary monitoring system integrated into a device for testing samples with at least one of an active/passive flow induction 27 and sample deposition port/pad of one embodiment. The monitoring system comprising at least one of a connector, monitor/detector, lysis function, active/passive flow induction 27 and sample deposition port/pad. FIG. 12 shows additional embodiments of the monitor 10 and associated receiver 12, whereby the monitor system 16 uses the processor 30, memory 32, communication circuitry 34 and power source 36 of the associated receiver. In this embodiment, the monitoring system 16 of FIG. 2 generally includes a connector 68, a monitor/detector component 20, a lysing function 69, an active/passive flow induction 27 and a sample deposition pad 71. The monitor/detector 20 comprising a plurality of sensors 28. It should be appreciated that some embodiments of the exemplary monitoring system may not require a lysing function 69 depending on the target analyte seeking to be monitored and measured. Similarly, some embodiments of the exemplary monitoring system may not require an active/passive flow induction 27.

In this embodiment, software stored in memory 32 can be in the form of an application, or "app" that can be downloaded from a central source such as an app store or the like. The app can be provided with various algorithms for determining test results. The app can be configured to be automatically updated with new algorithms as the need to detect particular analytes or various concentrations of analytes arise. That is, it is possible to provide new and/or additional algorithms for the app to generate test results.

FIGS. 13A and 13B illustrate an exemplary monitoring device and an exemplary monitoring system for monitoring a sample from an environment. The monitoring system comprising at least one of a connector, a monitor/detector, a lysis function, an active/passive flow induction 27 and a sample deposition port/pad. The associated receiver comprising a connector, processor, memory communication circuitry and a power source. In this embodiment, the exemplary sample is blood. However, it should be appreciated that a wide range of samples such as anterior nares, nasal mid-turbinate, nasopharyngeal, serum, sputum, saliva, sweat, tears, spinal fluid, urine, vaginal discharge among other bodily substances can be examined for the presence or absence analytes and measuring analyte concentration. Such samples can be collected from organisms such as humans or animals. In other embodiments, the test samples are collected from surfaces of any type for monitoring and detecting a wide range of chemical concentrations and analytes.

FIG. 13A shows for illustrative purposes only an example of an exemplary monitoring system with at least one of a connector, or a monitor/detector of one embodiment. The monitoring system comprising at least one of a connector, a monitor/detector, a lysis function, an active/passive flow induction 27 and a sample deposition port/pad. FIG. 13A shows a monitor 10, whereby the monitor 10 uses the processor 30, memory 32, communication circuitry 34 and power source 36 of the associated receiver 12. The monitor 10 comprising a connector 68, a monitor/detector 20, a lysing function 69, an active/passive flow induction 27 and a sample deposition pad 70. It should be appreciated that some embodiments of the exemplary monitoring system may not require a lysing function 69 depending on the target analyte seeking to be monitored and measured. Similarly, some embodiments of the exemplary monitoring system may not require an active/passive flow induction 27.

FIG. 13B shows for illustrative purposes an exemplary associated receiver that provides use of at least one component including a power source to the monitor of one embodiment. FIG. 13B shows the associated receiver 12 that provides use of at least one including the processor 30, memory 32, communication circuitry 34 or power source 36 to the monitor 10. The associated receiver 12 comprising a connector 68, a processor 30, memory 32, communication circuitry 34 and a power source 36.

Figure 14:
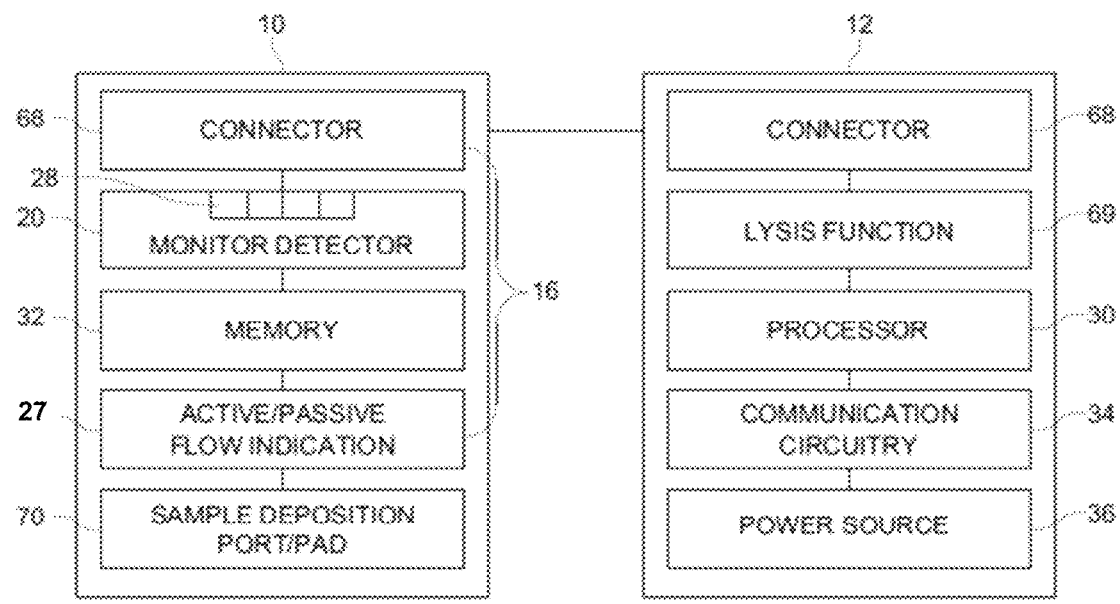
FIG. 14 shows a block diagram of an overview of an exemplary monitoring system integrated into a device for testing samples using a lysing function heater of one embodiment.

FIG. 14 shows a block diagram of an overview of an exemplary monitoring system integrated into a device for testing samples using a lysing function heater of one embodiment. The associated receiver comprising the lysis function. In this particular embodiment the lysing function is a heater. In another embodiment the lysis function includes a material for example buffers to solubilize the membrane proteins and to rupture the cell membrane to release its contents. However, it should be appreciated that a wide variety of lysing functions can be used including mechanical and non-mechanical methods. The monitor 10 comprising a connector 68, a monitor/detector 20, memory 32, an active/passive flow induction 27 and a sample deposition port/pad 70. The monitoring system 16 of FIG. 2 comprising a connector 68, monitor/detector 20, a plurality of sensors 28, memory 32 and an active/passive flow induction 27. The associated receiver 12 comprising a connector 68, a lysis function 69, a processor 30, communication circuitry 34 and a power source 36.

Like other exemplary embodiments, it should be appreciated that some embodiments of the exemplary monitoring system may not require a lysing function 69 depending on the target analyte seeking to be monitored and measured. Similarly, some embodiments of the exemplary monitoring system may not require an active/passive flow induction 27. In such a case, the monitor 10 comprising only a connector 68, monitor/detector 20, memory 32 and a sample deposition port/pad 70. The associated receiver 12 comprising only a connector 68, processor 30, communication circuitry 34 and a power source 36.

Figure 15:
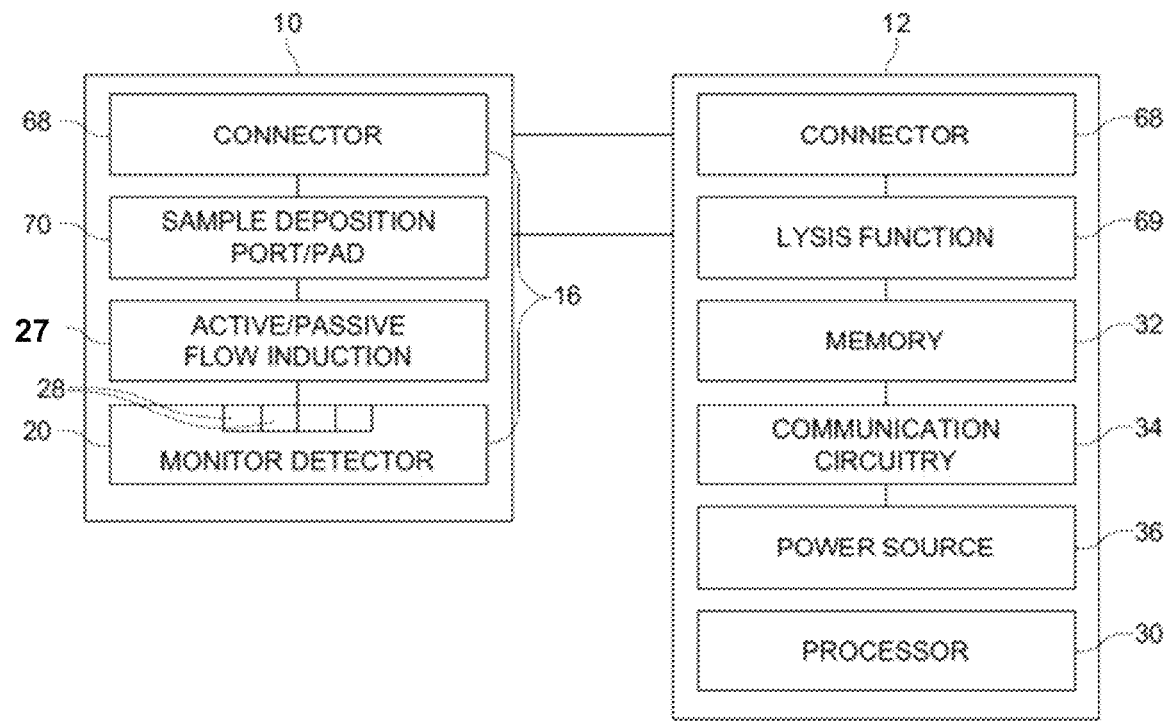
FIG. 15 shows a block diagram of an overview of an exemplary monitoring system integrated into a device for testing samples using the associated receiver memory of one embodiment.

FIG. 15 shows a block diagram of an overview of an exemplary monitoring system integrated into a device for testing samples using the associated receiver memory of one embodiment. The associated receiver includes the lysis function and memory. FIG. 15 shows another exemplary embodiment whereby the monitor 10 uses the processor 30, memory 32, communication circuitry 34 and power source 36 of the associated receiver 12. In this embodiment, the lysis function 69 is also part of the associated receiver 12. The monitor 10 and monitoring system 16 of FIG. 2 comprising a connector 68, a sample deposition port/pad 70, an active/passive flow induction 27 and a monitor/detector 20, whereby the monitor/detector 20 comprising a plurality of sensors 28. The associated receiver 12 comprising a connector 68, a lysis function 69, a memory 32, a communication circuitry 34, a power source 36 and a processor 30.

Like other exemplary embodiments, it should be appreciated that some embodiments of the exemplary monitoring system may not require a lysing function 69 depending on the target analyte seeking to be monitored and measured. Similarly, some embodiments of the exemplary monitoring system may not require an active/passive flow induction 27. In such a case, the monitor 10 comprising only a connector 68, sample deposition port/pad 70 and a monitor/detector 20. The associated receiver comprising only a connector 68, memory 32, communication circuitry 34, a power source 36 and a processor 30.

Figure 16:
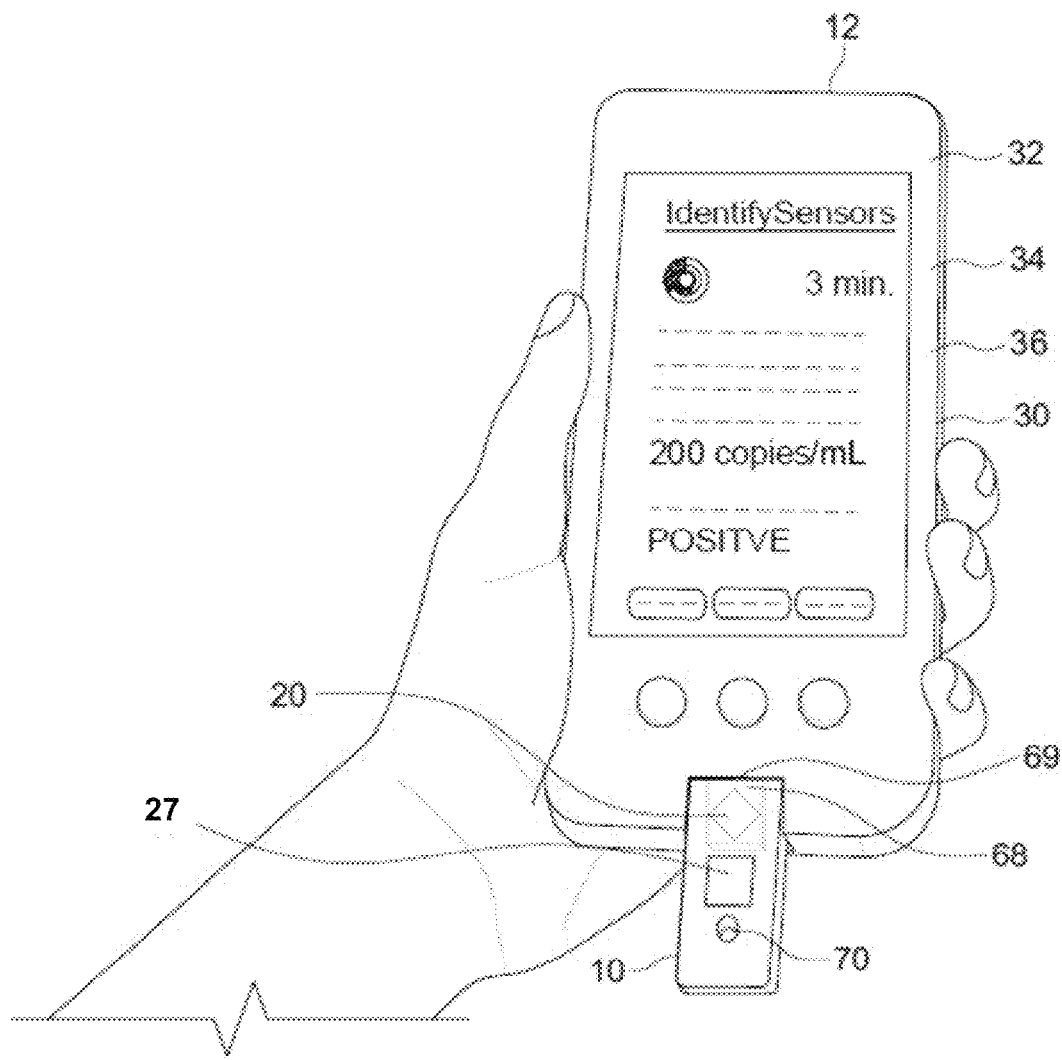
FIG. 16 shows for illustrative purposes only an example of an exemplary monitoring system selectively attachable to the associated receiver in the form of an electronic device of one embodiment.

FIG. 16 shows for illustrative purposes only an example of an exemplary monitoring system selectively attachable to the associated receiver in the form of an electronic device of one embodiment. FIG. 16 shows an exemplary monitoring system selectively attachable to the associated receiver in the form of a smartphone or like electronic device. The exemplary embodiment whereby the lysis function is part of the associated receiver 12. In this particular embodiment the lysis function is a heater configured to heat and control the temperature of the test sample before the test sample is presented to the monitor/detector 20. It should be appreciated that other methods of lysis function can be used such as mechanical and non-mechanical methods. The monitor 10 comprising a connector 68, a sample deposition port/pad 70, an active/passive flow induction 27 and a monitor/detector 20. The associated receiver 12 comprising a connector 68, a lysis function 69, a memory 32, communication circuitry 34, a power source 36 and a processor 30.

Like other exemplary embodiments, it should be appreciated that some embodiments of the exemplary monitoring system may not require a lysing function 69 depending on the target analyte seeking to be monitored and measured. Similarly, some embodiments of the exemplary monitoring system may not require an active/passive flow induction 27. In such a case, the monitor 10 comprising only a connector 68, sample deposition port/pad 70 and a monitor/detector 20. The associated receiver comprising only a connector 68, memory 32, communication circuitry 34, a power source 36 and a processor 30.

FIGS. 17A-17D illustrate various methods and configurations for sampling an environment or surface. It will be appreciated that the present disclosure is not limited to any method, design or configuration for sampling an environment or surface and that aspects of the disclosure can be embodied in a wide variety of sampling methods.

FIG. 17A illustrates an exemplary monitoring system integrated into a strip that is placed at the source of a test sample of one embodiment. In one embodiment, the strip is placed at the source of the test sample for a direct reading from the monitor/detector. In another embodiment, the sample collector 71 is converted to a vacuum using either a power source or a spring drawing air from the sample source to the monitor/detector for a direct reading.

FIG. 17B shows for illustrative purposes only an example of sampling a medium sized surface area with the tip of the sample collector of one embodiment. FIG. 17B shows a method for sampling a medium sized surface area using a sample collector 71. In this embodiment, the tip of the sample collector 71 covers a medium sized surface area. The embodiment of the medium sized surface area sample collector draws a larger sample as compared to the sample obtained and described in FIG. 17A. The purpose of the medium sized surface area sample collector is to sample from a larger surface area.

FIG. 17C shows for illustrative purposes only sampling a large sized surface area using a sample collector of one embodiment. FIG. 17C shows a method for sampling a large sized surface area using a sample collector 71. The large sized surface area embodiment of the sample collector 71 further increases the probability of detecting an analyte if present. Multiple large sized surface area sample collector 71 can be given identifying numbers to correlate with grid coordinates of a larger surface area. Any analyte detected can thereby be located within the large surface area grid for further processing and disinfection.

FIG. 17D shows for illustrative purposes only an example of sampling liquid from an environment or surface with a syringe used to collect bodily fluid samples of one embodiment. FIG. 17D shows a method for sampling liquid from an environment or surface. In the exemplary embodiment, a syringe is used to collect bodily fluid samples such as saliva, sweat, sputum, urine, vaginal discharge, blood among other human and animal bodily fluids. It will be appreciated that a wide variety of syringes, swabs, cups, vials and collectors are envisioned to be used in the collection of samples. In one embodiment, a syringe with a needle is used for collecting blood, plasma and other bodily fluids. In other embodiment's syringes, vials and cups of various arrangements are used to collect saliva, sweat, sputum, urine, vaginal discharge and other bodily fluids.

In the exemplary embodiments presented in FIGS. 17A-17D the sample collector 71 can comprise a wide range of materials such as cotton, flocked, cloth, nanofiber and other nanomaterials or nanoscale fibers. In one embodiment, nanofiber swabs tipped with hierarchical 3D nanofiber objects are produced by expanding electrospun membranes with a solids-of-revolution-inspired gas foaming technique. Nanofiber swabs significantly improve adsorption and release of proteins, cells, bacteria, DNA and viruses from solutions and surfaces.

It is to be appreciated that the exemplary embodiments in FIGS. 17A-17D are also amendable to other like applications such as embedding monitors 10 or monitoring systems 16 into the sample collector 71 such that a separate monitor 10 or monitoring system 16 of FIG. 2 is not required.

Figure 18B:
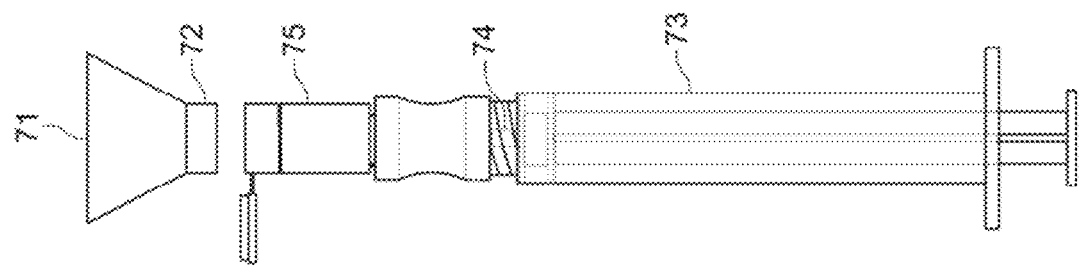
FIG. 18B shows for illustrative purposes three sample collector components with the cup or funnel disconnected from the collection assembly of one embodiment.
Figure 18A:
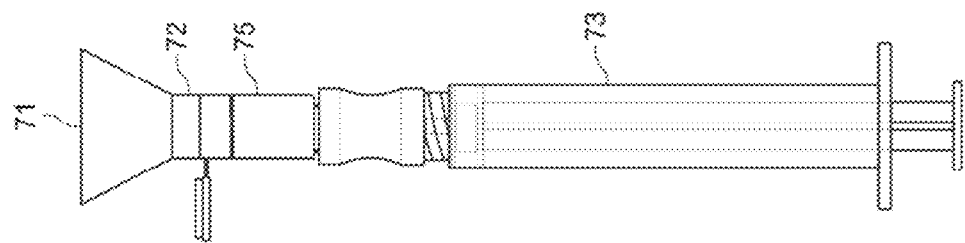
FIG. 18A shows for illustrative purposes an example of a sample collection cup or funnel adapted to fit within the collection vial assembly connected to the syringe of one embodiment.

FIGS. 18A-18B presents an exemplary sample collector 71 comprising a sample collection cup or funnel 72, a syringe 73, a connector 74 and a sample collection assembly 75. The syringe 73 is selectively attachable to the sample collection assembly 75 and the monitor 10 or monitoring system 16 of FIG. 2 through a connector 74 in the form of a luer lock tip. The cap of the sample collection assembly 75 has a small vent hole to allow sample removal. In other embodiments, a filter for filtering the test sample can be part of the sample collection cup or funnel 72 or be part of the collection assembly 75 or be part of the syringe 73.

FIG. 18A shows for illustrative purposes an example of a sample collection cup or funnel adapted to fit within the collection vial assembly connected to the syringe of one embodiment. FIG. 18A shows the sample collection cup or funnel 72 connected to the syringe 73 using a collection assembly 75 and a connector 74. The collection funnel 72 is adapted to fit within the collection vial assembly 75. The collection vial assembly 75 has a cap with a luer activated valve on the bottom to prevent leakage during collection and disposal. The collection vial assembly 75 also has a small vent hole to allow sample removal while minimizing the potential for spillage. The funnel 72 channels the test sample into the collection assembly 75 and upon the collection of adequate sample volume, the cap of the collection assembly 75 is put in place allowing the collected sample to be drawn into the syringe 73 by pulling the syringe plunger. After transferring adequate test sample volume to the syringe 73, the syringe is released from the collection assembly 75 through the connector 74 and connected to the sample deposition port/pad 70 of the monitor 10 using a luer lock connection mechanism 74.

FIG. 18B shows for illustrative purposes three sample collector components with the cup or funnel disconnected from the collection assembly of one embodiment. FIG. 18B shows three sample collector components with the cup or funnel 72 disconnected from the collection assembly 75 and the collection assembly 75 disconnected from the syringe 73 with a connector 74 in the form of luer lock. It will be appreciated that the present disclosure is not limited to any method of or design for connecting the sample collection cup or funnel 72 to a collection assembly 75 and a syringe 73, whereby the syringe is selectively attachable to the monitor 10 or to monitoring system 16 of FIG. 2. In another embodiment, the sample collection cup or funnel 72 is inserted in the plunger end of the syringe such that the test sample flows from the collection funnel into the syringe settling above the luer lock tip of the syringe. In this embodiment the collection assembly is not used. Aspects of the disclosure can be embodied in a wide variety of both attachment components as well as devices for collecting a test sample. In other embodiments, aspects of the disclosure can be embodied in other types of sample collection methods commonly used for collecting bodily samples. For example, sample collection vials, tubes, swab, cups, collectors and the like. Other examples include wearable or implantable devices such as mouthpieces, pacifiers, retainers and the like as well as any other type of device that can be deposited or attached or embedded in a body for collecting a bodily sample. Devices deposited in body parts such as mouth, ear, nose, throat, anal cavity, vagina, or the like are particularly applicable to the exemplary embodiment.

Figure 19:
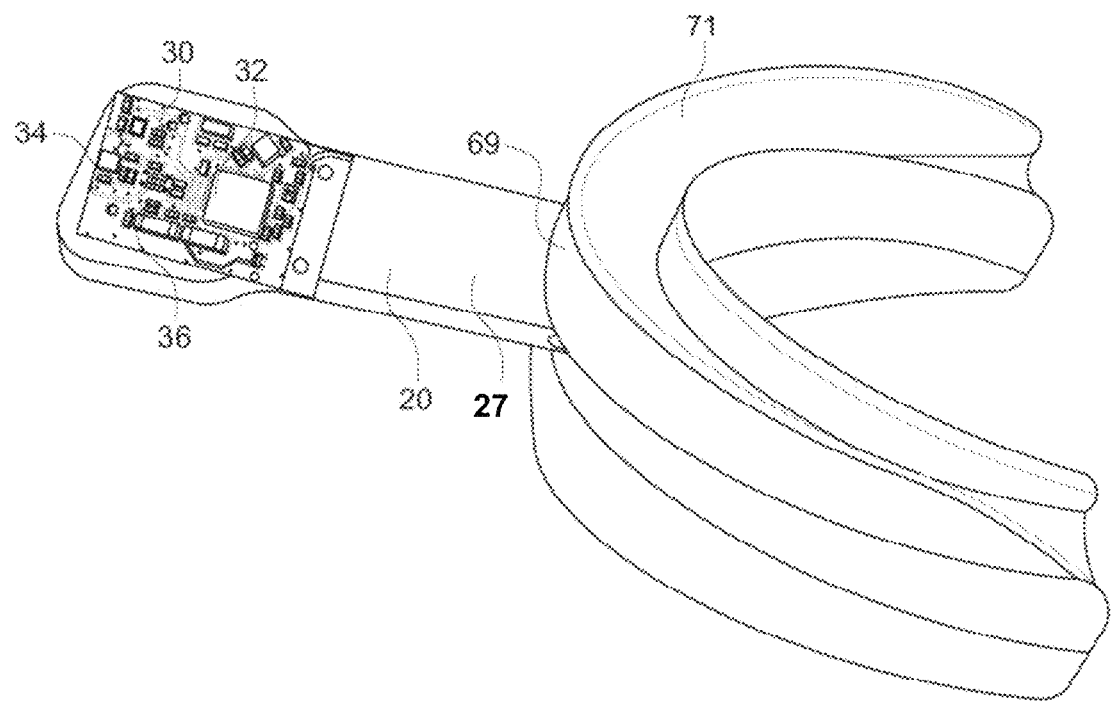
FIG. 19 shows for illustrative purposes a monitoring system integrated into the sample collector in the form of a mouthpiece of one embodiment.

FIG. 19 shows for illustrative purposes only a monitoring system integrated into the sample collector in the form of a mouthpiece of one embodiment. In the exemplary embodiment the sample collector 71 is in the form of a mouthpiece, which collects the test sample. The test sample then flows through the active/passive flow induction 27 component through the lysis function 69 then onto the monitor/detector 20 where a plurality of sensors 28 of FIG. 2 are used to monitor or measure analytes. In the exemplary embodiment, components of the associated receiver are integrated into the stem of the mouthpiece or like component. For example, the processor 30, memory 32, communication circuitry 34 and the power source 36 are all integrated into the stem of the mouthpiece such that the mouthpiece generates data in response to the presence or absence of at least one analyte or concentration of one analyte and communicate the data to an associated personal communication device or the like for processing. The data is processed through a Cloud-based app stored in memory of the associated personal communication device or like for processing.

In yet another exemplary embodiment, the monitoring system integrated into a mouthpiece comprising a connector 68 of FIG. 10 configured for connecting to a port or connector of the personal communication device such that the monitoring system integrated into a mouthpiece uses the processor 30, memory 32, communication circuitry 34 and power source 36 of the associated personal communication device to generate test data and transmit that data through a Cloud-based app stored in memory of the associated personal communication device or like device for processing.

Figure 20:
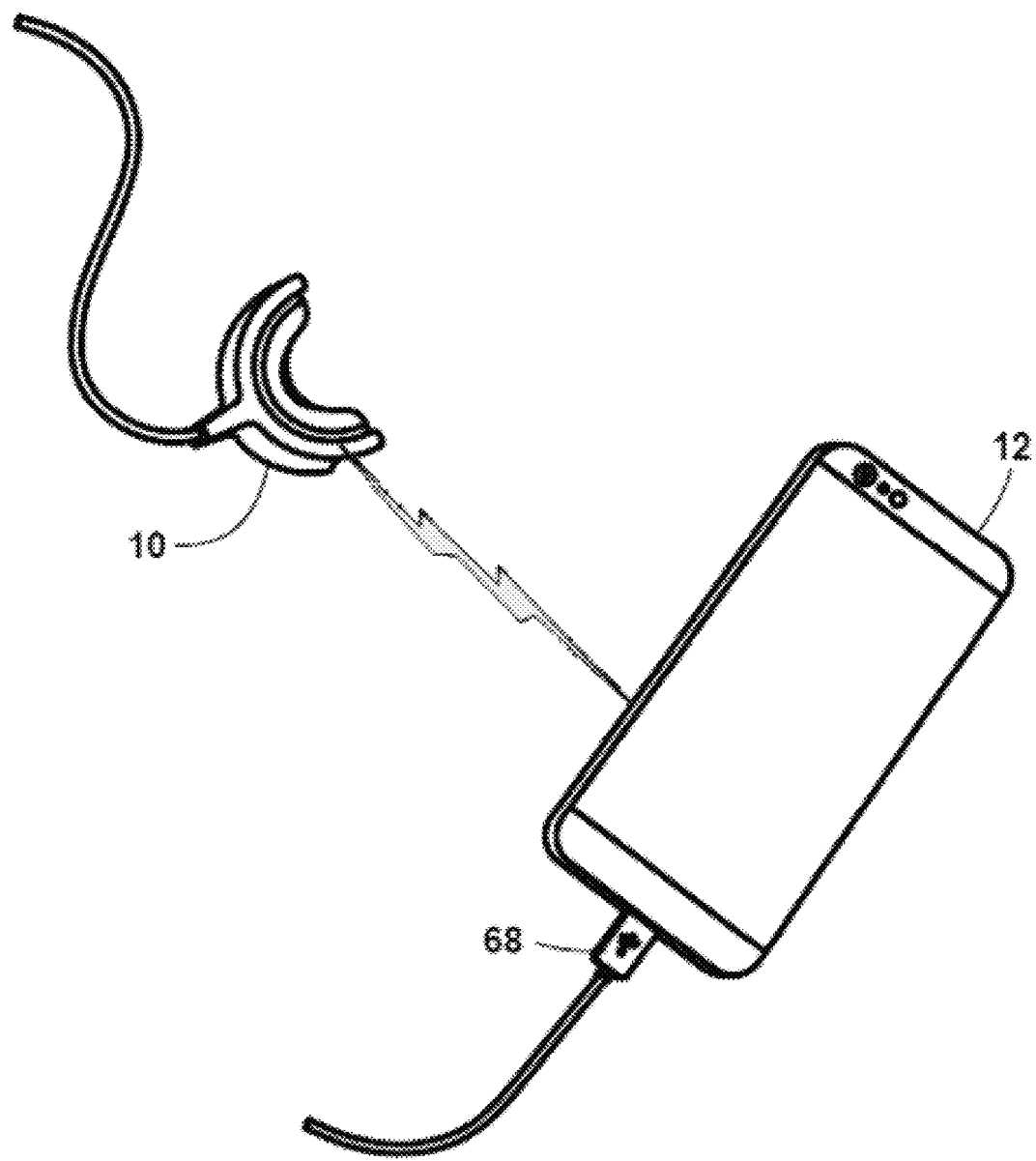
FIG. 20 shows for illustrative purposes an exemplary monitoring system integrated into a mouthpiece that connects to a smartphone of one embodiment.

FIG. 20 shows for illustrative purposes an exemplary monitoring system integrated into a mouthpiece that connects to a smartphone of one embodiment. The monitor 10 in the form of a mouthpiece can comprise of any combination or arrangement of previously disclosed components such as a connector, monitor/detector, memory, lysis function and active/passive flow induction 27. In the exemplary embodiment, the connector 68 is in the form of a power cable that connects the monitor 10 directly to the smartphone 12.

Figure 21:
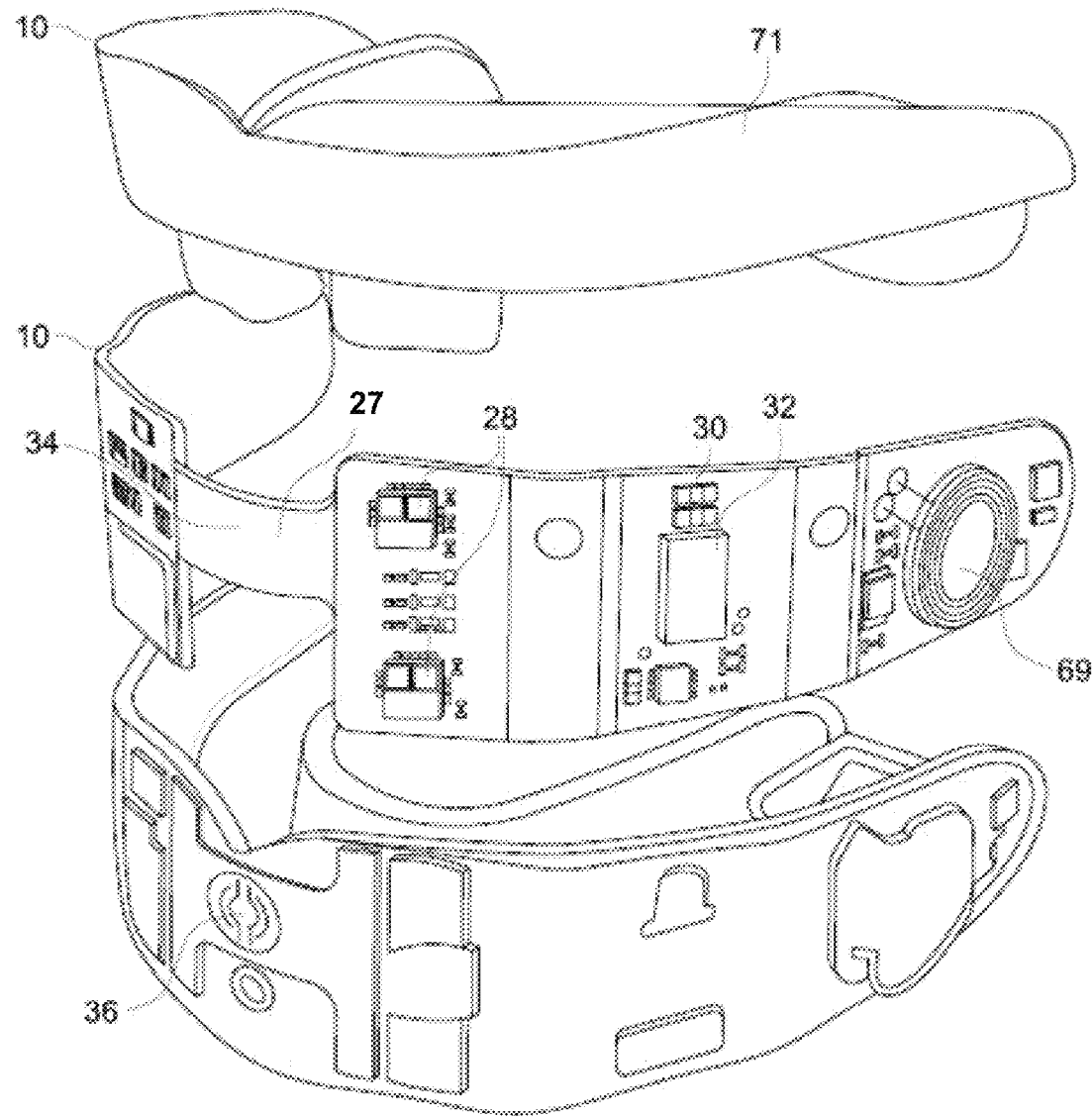
FIG. 21 shows for illustrative purposes an exemplary monitoring system integrated into a mouthpiece that wirelessly connects with the associated receiver of one embodiment.

FIG. 21 shows for illustrative purposes an exemplary monitoring system integrated into a mouthpiece that wirelessly connects with the associated receiver. In the exemplary embodiment the sample collector 71 is in the form of a mouthpiece, which collects the test sample. The monitor 10 comprising a monitor/detector 20, a memory 32, a lysis function 69, and an active/passive flow induction 27. The associated receiver comprising a processor 30, memory 32, communication circuitry 34 and a power source 36. In the exemplary embodiment, the monitor 10 connects electrically or wirelessly to the associated receiver 12 in the form of a smart device or like device for processing. Similar to other exemplary embodiments, it should be appreciated that some embodiments of the exemplary monitoring system may not require a lysing function 69 depending on the target analyte seeking to be monitored and measured. Similarly, some embodiments of the exemplary monitoring system may not require an active/passive flow induction 27 or a memory 32. In such a case, the monitor 10 comprising only a monitor/detector 20 of FIG. 2. The associated receiver comprising only a processor 30, memory 32, a plurality of sensors 28, communication circuitry 34 and a power source 36.

Figure 22:
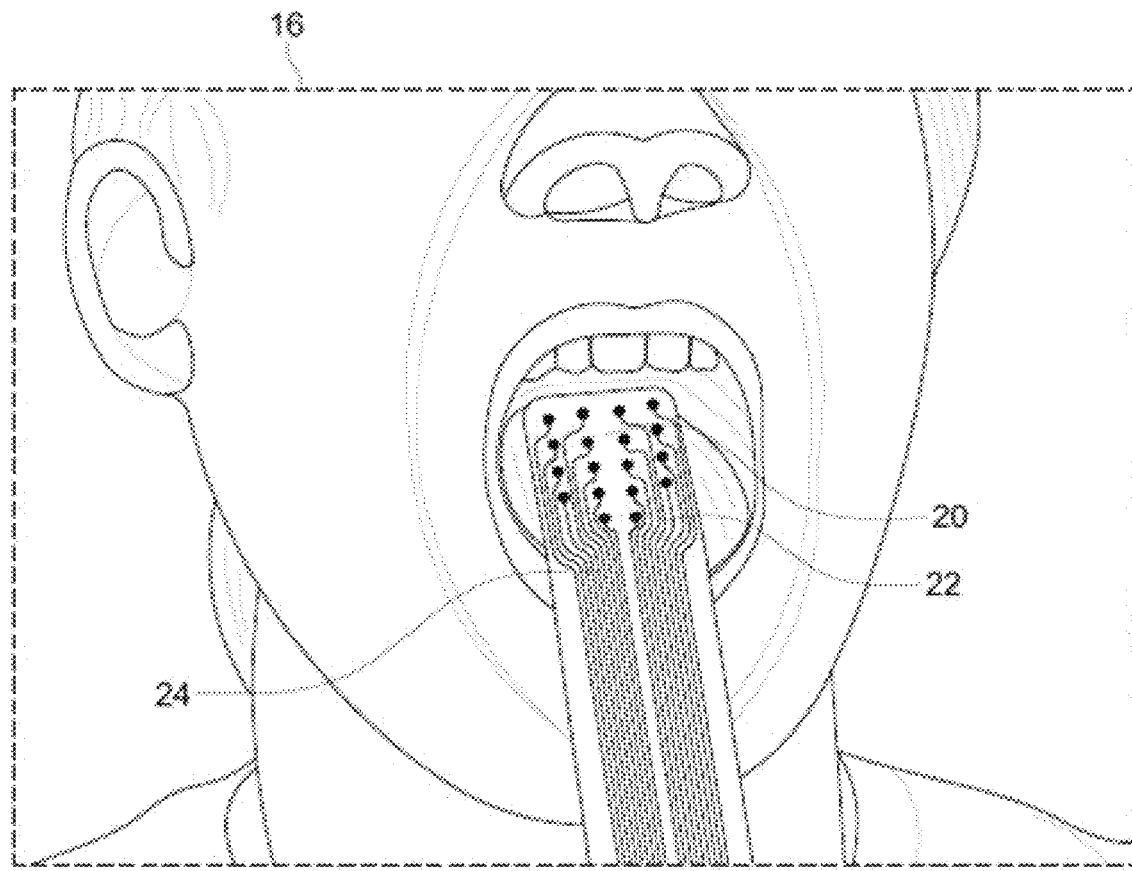
FIG. 22 shows for illustrative purposes an exemplary monitoring system placed in a bodily opening such as a mouth of one embodiment.

FIG. 22 shows for illustrative purposes an exemplary monitoring system placed in a bodily opening such as a mouth of one embodiment of one embodiment. In the exemplary embodiment, the bodily opening is a mouth and the monitoring system 16 is in the form of a culture stick. The monitoring system 16 comprising communication circuitry 22, a power source 24 and a monitor/detector 20, can comprise a plurality of sensors 28 of FIG. 2. In this exemplary embodiment, an active/passive flow induction 27 of FIG. 10 is not required. However, it is to be appreciated that the exemplary embodiment may also be amenable to use of an active/passive flow induction 27 of FIG. 10 configured to direct a flow of air or liquid to the detector component.

The power source 24 can be at least one of a battery, a photovoltaic cell or an antenna for receiving electromagnetic energy. At least one of the detector components 20, communication circuitry 22 or power source 24 can be part of a removable/replaceable module selectively attachable to the culture stick.

In accordance with previously disclosed embodiments, the monitoring system 16 generates data indicative of the presence or absence of an analyte in the environment and transmits that data to an associated receiver in the form of a cell phone 12. The data is processed using Cloud-based software and can be in the form of an application, or an "app", that is downloaded from an app store or the like. The app can be provided with various "algorithms" for determining concentrations of analytes. The algorithms can be used to determine whether the analyte was detected by the monitoring system 16. The app can be configured to be automatically updated with new algorithms as the need to detect particular analytes as they arise. That is, it is possible to provide new and/or additional detection algorithms for the app to monitor and measure specific analytes.

The monitor system further includes communication circuitry 22 and a power source 24. The communication circuitry 22, in one embodiment, includes at least one of a near field communication device, Bluetooth communication device, cellular communication device, satellite communication device, WIFI communication device, or any other suitable communication circuitry for establishing communications with an associated receiver or cell phone 12. The power source 24 can be a power supply such as a battery (lithium or other). In other embodiments, the power source 24 can be an antenna configured to receive energy wirelessly and supply the received energy to one or both of the monitor/detector component 20 and/or communication circuitry 22 such that no onboard battery is required for operation of the monitor system 16. In still other arrangements, the power source 24 can be a connector configured to couple with a port of the associated receiver or cell phone 12 to receive power from a power source of the smartphone 12.

While the foregoing embodiments illustrate a monitoring system generating data in response to the presence or absence of at least one analyte in a bodily opening such as a mouth or the like, it should be appreciated that the monitoring system of the above-described embodiments can also be configured in other ways by being physically attached thereto. Thus, the monitoring system can be provided as a standalone system to which the personal communication device can be configured to connect to perform the above-described functions.

Figure 23:
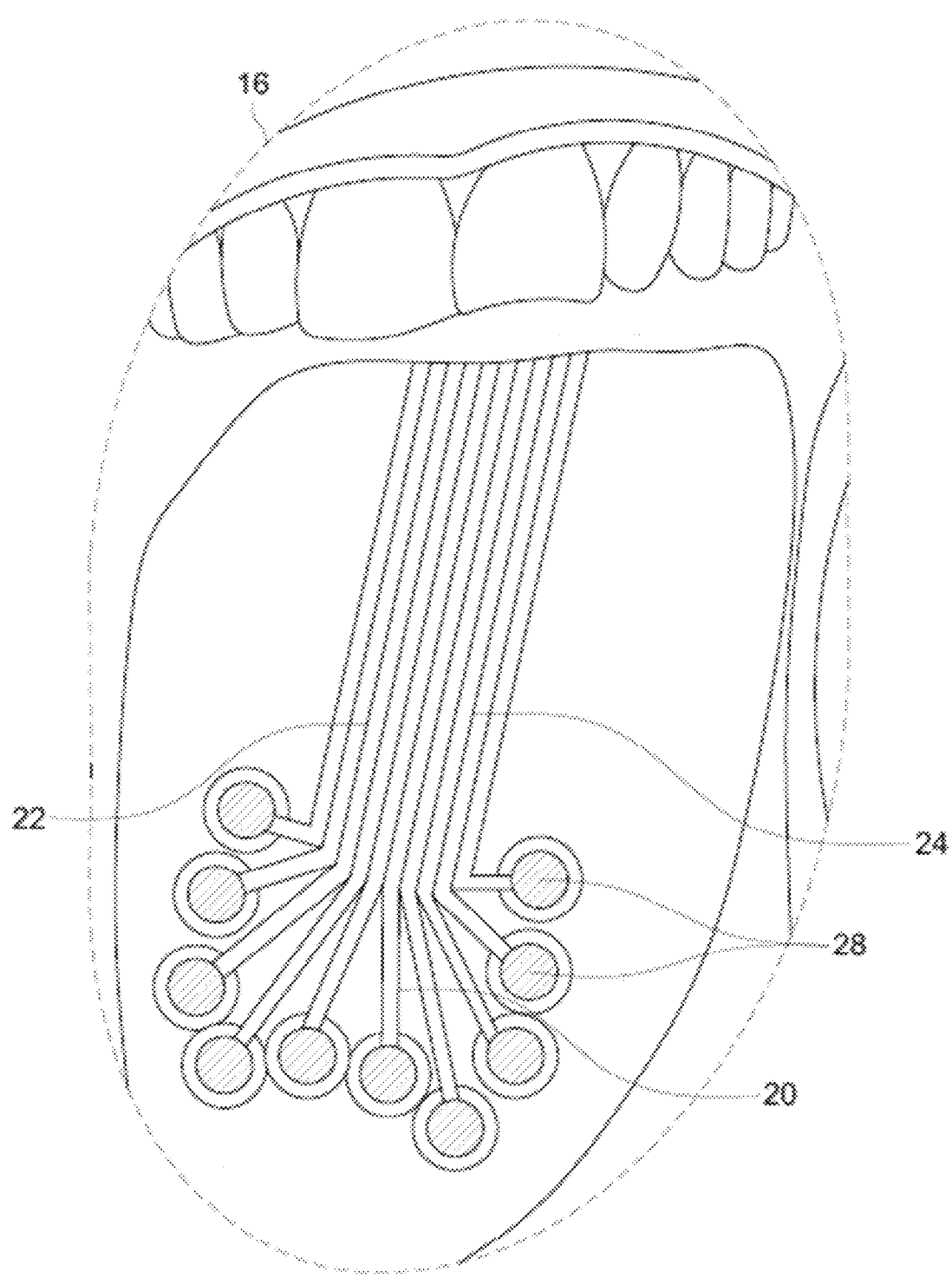
FIG. 23 shows for illustrative purposes only an example of an exemplary monitoring system in the form of a thin film applied to the surface of a tongue of one embodiment.
Figure 24:
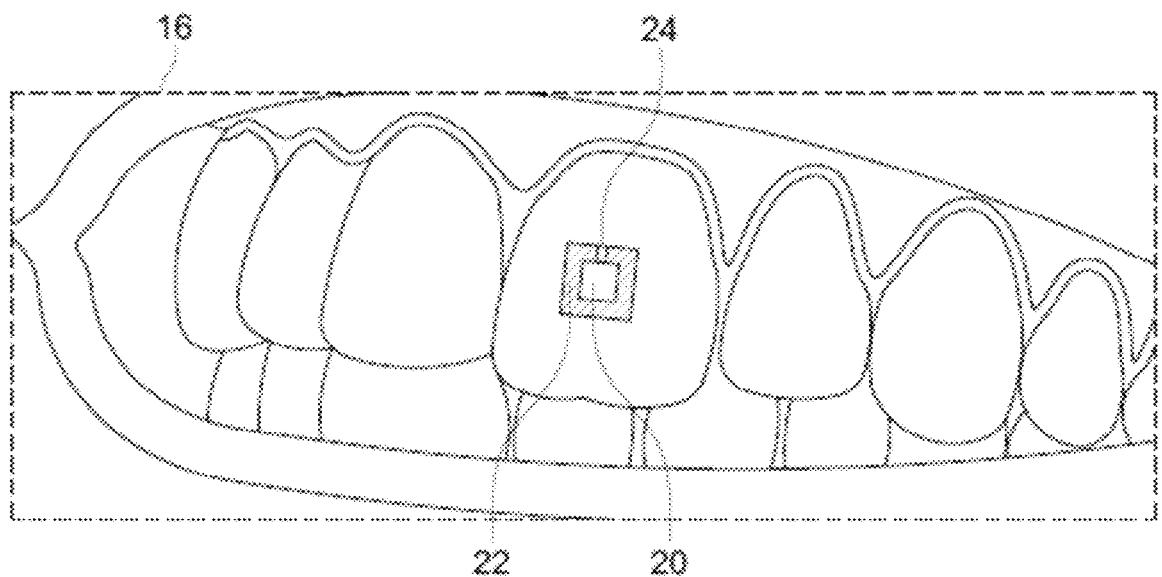
FIG. 24 shows for illustrative purposes an exemplary monitoring system on a tooth inside of a mouth of one embodiment.

For example, with reference to FIG. 23 and FIG. 24, a monitoring system is attached to areas or surfaces inside of a mouth, such that the monitoring system 16 is in direct contact with a bodily fluid such as saliva, sputum or other bodily substances.

FIG. 23 shows for illustrative purposes only an example of an exemplary monitoring system in the form of a thin film applied to the surface of a tongue of one embodiment. It should be appreciated that the thin film is applied to the tongue in any suitable manner such that an adequate volume of bodily fluid test sample is presented to the monitor/detector 20. Exemplary methods of applying the thin film include tattoo, sticker or other suitable methods.

With reference to FIG. 23, the monitoring system 16 generally includes a monitor/detector component 20, communication circuitry 22 and a power source 24. It should be appreciated that the monitor/detector component 20 can comprise a plurality of sensors 28 and that the monitoring system 16 can be deployed in suitable locations throughout a body. The power source 24 can be a power supply such as a battery (lithium or other). In other embodiments, the power source 24 can be an antenna configured to receive energy wirelessly and supply the received energy to one or both of the monitor/detector component 20 and/or communication circuitry 22 such that no onboard battery is required for operation of the monitor system 16.

FIG. 24 shows for illustrative purposes only an example of an exemplary monitoring system on a tooth inside of a mouth of one embodiment. The monitoring system 16 generally includes a monitor/detector component 20, communication circuitry 22 and a power source 24. It should be appreciated that the monitor/detector component 20 can comprise a plurality of sensors 28 of FIG. 2 and the power source 24 can be a power supply such as a battery (lithium or other). In other embodiments, the power source 24 can be an antenna configured to receive energy wirelessly and supply the received energy to one or both of the monitor/detector component 20 and/or communication circuitry 22 such that no onboard battery is required for operation of the monitor system 16.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The foregoing has described the principles, embodiments and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. A system for monitoring an environment, comprising:
  a monitoring device coupled to an associated receiver to receive power from a power source of the associated receiver, a lysis function to rupture membranes of cells in a collected sample and release the cell contents, a monitor detector having a plurality of sensors to detect at least one analyte of the contents of the sample, and a memory device to record sensor data;
  a detector component coupled to the monitoring device configured to detect at least one analyte signature data, a concentration of the detected analyte signature data and environment information related to an environment;
  a location device coupled to the detector component configured to record a detection location of the detector component at a time of detection of the at least one analyte signature data and the environment information;
  a first memory device coupled to the detector component configured to receive and record data comprising operating status of the detector component and, at the time of detection, the detected at least one analyte signature data, the concentration of the detected analyte signature data and the environment information;
  at least one communication device coupled to the detector component configured to transmit the recorded data to the associated receiver, wherein the associated receiver is configured to receive and process the recorded data;
  an active/passive flow induction device coupled to the detector component configured to direct a flow of air or liquid to the detector component; and
  wherein at least one of the detector component, the communication circuitry, the power source or the lysis function is a printed component.

2. The system of claim 1, wherein the associated receiver includes at least one of a personal communication device or electronic device or wearable or peripheral device or smart device or smart infrastructure.

3. The system of claim 1, further comprising a housing configured to couple selectively directly to an associated receiver or to a protective case of an associated receiver.

4. The system of claim 1, wherein the housing is selectively attachable directly to an associated receiver or to a protective case of an associated receiver.

5. The system of claim 1, wherein the printed component is configured to be supported on an adhesively backed substrate.

6. The system of claim 1, wherein the printed component is coupled to an adhesively backed substrate and is further configured to be coupled to at least one of an animal collar or muzzle, a vehicle or a drone or a robot or a checkpoint, area where cargo is stored, area where food is stored or transported or displayed, public space or restroom, box or luggage or freight, air ducts or liquid flow conduits of infrastructure or a hand-held wand or a bodily opening or a surgical surface or a food processing surface.

7. An apparatus comprising:
  a monitoring device having a collection area to collect a sample and a lysis function, wherein the lysis function is configured to rupture membranes of cells in a sample to release the contents of the cell into the sample;
  a detector component coupled to the monitoring device having a plurality of sensors to detect at least one analyte of the contents of the sample and configured to detect at least one analyte signature data, a concentration of the detected analyte signature data and environment information related to an environment;
  wherein the monitoring device further includes an active/passive flow induction device configured to direct fluid flow to the detector component and a sample deposition port/pad configured to transfer the sample to the detector component for monitoring and measuring analytes;
  a location device coupled to the detector component configured to record a detection location of the detector component at a time of detection of the at least one analyte signature data and the environment information;
  a first memory device coupled to the detector component configured to receive and record data comprising operating status of the detector component and, at the time of detection, the detected at least one analyte signature data, the concentration of the detected analyte signature data and the environment information; and
  at least one communication circuitry coupled to the detector component configured to transmit the recorded data to an associated receiver, wherein the associated receiver is configured to receive and process the recorded data.

8. The apparatus of claim 7, wherein the associated receiver includes a non-transitory computer readable medium configured to store instructions causing a processor to execute an application to process the data, wherein the application is configured to receive the data or information from the monitoring device; and analyze the data to detect or interpret one or more analyte signatures.

9. The apparatus of claim 7, further comprising a housing configured to selectively attach to the associated receiver.

10. The apparatus of claim 7, further comprising at least one component coupled to the associated receiver including at least one of a processor, at least one memory device, communication circuitry and power source, at least one peripheral device wirelessly coupled to the associated receiver having a monitoring device for monitoring an environment, wherein the monitoring device is configured to generate detection data of at least one of an analyte signature or a chemical in the environment and wirelessly communicate the data to the associated receiver.

11. The apparatus of claim 7, further comprising an active/passive flow induction device coupled to the detector component configured to direct flow of air or liquid to the detector component.

12. The apparatus of claim 7, wherein at least one of the detector component, communication circuitry, power source or lysis function is a printed component, wherein the printed component is at least one of a screen printed element or aerosol printed element or offset printed element or gravure printed element or a flexographic printed element or lithographic printed element or spin/spray coating printed element or a pad-printed element or an ink-jet printed element or a digital printed element or 3D printed element.

13. The apparatus of claim 12, wherein the printed component is configured to be supported on an adhesively backed substrate.

14. A method of detecting an analyte, comprising:
providing a monitoring device having a power source and configured to rupture membrane cells in a sample to release the cell contents, to record sensor data and to transfer the sample from a sample collector to a monitor detector for monitoring and measuring analyte concentrations of the contents with a sample deposition port/pad coupled to the sample collector;
providing a detector component having a plurality of sensors coupled to the monitoring device to detect from the contents of the sample at least one analyte signature data and environment information related to an environment and to direct fluid flow to the detector component with an active/passive flow induction device;
recording a detection location of the detector component at a time of detection of the at least one analyte signature data and the environment information;
receiving and recording data comprising operating status of the detector component and, at the time of detection, the detected at least one analyte signature data and the environment information; and
providing a communication device coupled to the detector component for transmitting the recorded data to an associated receiver, wherein the associated receiver receives and processes the recorded data.

15. The method of claim 14, wherein the associated receiver is configured to be remote and spaced apart from the monitoring device.

16. The method of claim 14, wherein providing the detector component includes communicating wirelessly to the associated receiver the data or information.

17. The method of claim 14, further comprising providing at least one wireless communication device having at least one of WIFI, cell, Bluetooth, near-field communication, satellite, infrared, optical, sonic, ultrasonic, electromagnetic, broadcast radio, microwave or very low frequency radiation component for communicating the data to the associated receiver.

18. The method of claim 14, further comprising positioning the monitoring device in or on at least one of an animal collar or muzzle, a vehicle or a drone or a robot or a checkpoint, area where cargo is stored, area where food is stored or transported or displayed, public space or restroom, box or luggage or freight, air ducts or liquid flow conduits of infrastructure or a hand-held wand or a bodily opening or a surgical surface or a food processing surface.

19. The method of claim 14, wherein the detector component is further configured to detect a concentration of at least one chemical in the environment and wirelessly transmit the detected chemical concentration to the associated receiver.

* * * * *